United States Patent [19]
Mazer et al.

[11] Patent Number: 5,755,689
[45] Date of Patent: *May 26, 1998

[54] APPARATUS FOR ADDING MARKER DYE TO NUTRITIONAL PRODUCT DURING ENTERAL TUBE FEEDING

[75] Inventors: Terrence Bruce Mazer, Reynoldsburg; Joseph Edward Walton, Westerville; Ronita Kay Geckle, Columbus; Carl Joseph Piontek, Powell, all of Ohio; Susan Beth Duel, Laurinburg, N.C.; Andre Daab-Krzykowski; Robert Louis Joseph, both of Columbus, Ohio; William Guy Pierson, Canal Winchester, Ohio; Thomas Daniel Loughrin, Columbus, Ohio; Thomas Walter Osip, Dublin, Ohio

[73] Assignee: Abbott Laboratories, Abbott Park, Ill.

[*] Notice: The term of this patent shall not extend beyond the expiration date of Pat. No. 5,531,682.

[21] Appl. No.: 671,876
[22] Filed: Jun. 28, 1996

Related U.S. Application Data

[63] Continuation of Ser. No. 372,266, Jan. 13, 1995, Pat. No. 5,531,682.

[51] Int. Cl.⁶ ................................................. A61M 37/00
[52] U.S. Cl. .................. 604/84; 604/83; 604/890.1; 604/8; 604/85
[58] Field of Search ........................ 604/82–85, 92, 604/252, 257, 258, 270, 403, 404, 411, 416, 892.1, 8; 128/653.4, 654

[56] References Cited

U.S. PATENT DOCUMENTS

| | | | |
|---|---|---|---|
| 4,390,017 | 6/1983 | Harrison et al. | 604/270 |
| 4,511,353 | 4/1985 | Theeuwes | 604/85 |
| 4,927,411 | 5/1990 | Pastrone et al. | 604/65 |
| 4,985,017 | 1/1991 | Theeuwes | 604/84 |
| 5,069,671 | 12/1991 | Theeuwes | 604/251 |
| 5,318,558 | 6/1994 | Linkwitz et al. | 604/892.1 |
| 5,324,280 | 6/1994 | Wong et al. | 604/892.1 |
| 5,385,545 | 1/1995 | Kriesel et al. | 604/82 |
| 5,385,546 | 1/1995 | Kriesel et al. | 604/85 |
| 5,484,410 | 1/1996 | Kriesel et al. | 604/89 |

OTHER PUBLICATIONS

Potts et al., "Comparison of Blue Dye Visualization and Glucose Oxidase Test Strip Methods for Detecting Pulmonary Aspiration of Enteral Feeding in Intubated Adults," Chest, vol. 103, Jan. 1993, pp. 117–121.

"Nutrition in Critical Care," Zaloga, ed., 1994, pp. 439–467.

*Primary Examiner*—Michael Powell Buiz
*Assistant Examiner*—Deborah Blyveis
*Attorney, Agent, or Firm*—Brian R. Woodworth

[57] ABSTRACT

An apparatus is useful for dye marking a liquid enteral nutritional product during delivery thereof from a supply container to a feeding tube delivering the nutritional product to the gastrointestinal tract of a patient. A formulation chamber, such as a drip chamber, is connectable to the supply container. At least one sustained release reservoir containing a physiologically acceptable marker dye is positioned within the formulation chamber, or if not, is included as part of a kit. The sustained release reservoir may be in the form of a coated tablet, osmotically driven device, coated capsule, microencapsulated microspheres, agglomerated molecular sieving material, or chopped hollow fibers having permeable walls. A liquid communication means connects the formulation chamber to the feeding tube of a patient. The marker dye may be a colorant dye or a fluorescing dye or a mixture thereof. In using the apparatus for dye marking the nutritional product is flowed through the apparatus and a feeding tube to enter the gastrointestinal tract of a patient.

30 Claims, 13 Drawing Sheets

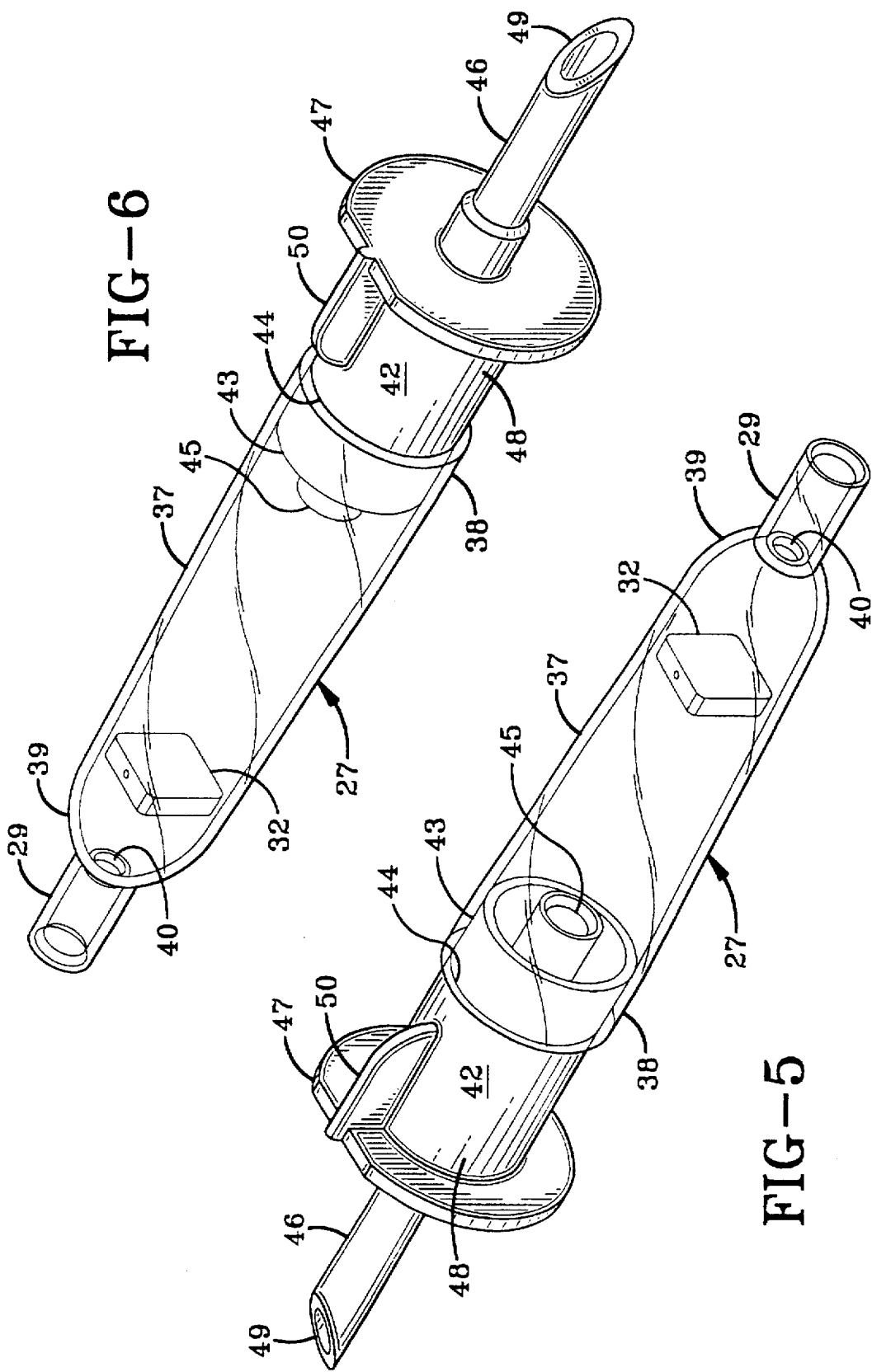

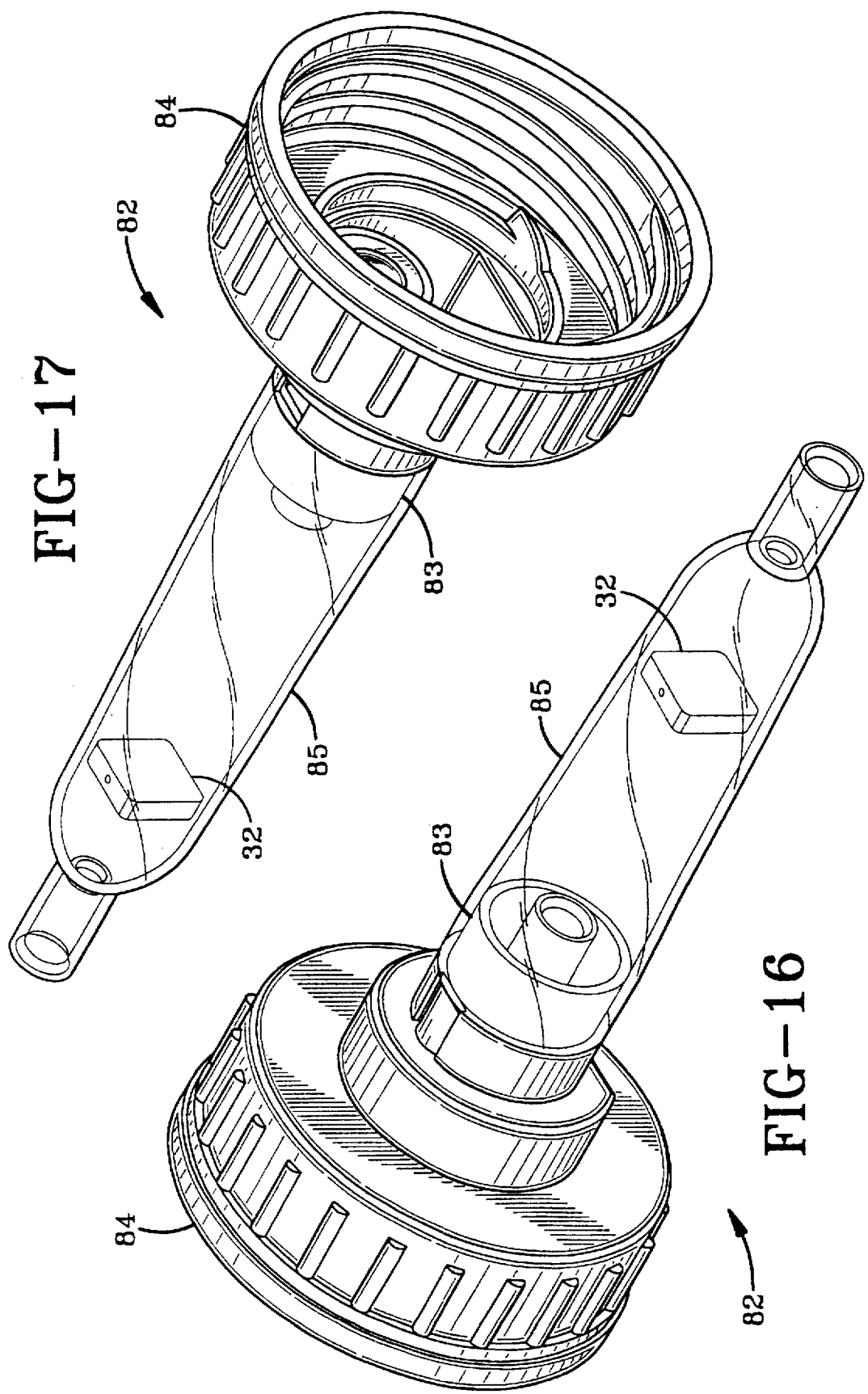

APPARATUS FOR ADDING MARKER DYE TO NUTRITIONAL PRODUCT DURING ENTERAL TUBE FEEDING

This is a continuation of application Ser. No. 08/372,266, filed Jan. 13, 1995, now U.S. Pat. No. 5,531,682.

FIELD OF THE INVENTION

The invention relates to an apparatus for feeding liquid enteral nutritional products and particularly to modifying a liquid enteral nutritional product having a viscosity in the range of from 1 to about 300 centipoises (cps.) during the feeding thereof into the gastrointestinal tract of a patient to make the flow of the product more easily visually detected.

BACKGROUND OF THE INVENTION

The feeding of a liquid enteral nutritional product from a container, such as a bottle or a plastic bag with a bottom outlet connecting to a drip chamber and the latter to a flexible tubing, or lumen, leading to a nasogastric tube or a feeding tube inserted through a gastrostomy or a jejunostomy, by gravity flow or aided by a peristaltic pump, is well known. The liquid enteral nutritional product may be aseptically processed or terminally retorted before use, and may be supplied in a pre-filled, ready-to-hang container, or placed in such a container by a caregiver. However, problems sometimes arise that the flow of the liquid enteral nutritional product is not begun because of a mechanical malfunction or distraction of the caregiver and this is not noted for a time. Sometimes the product is misdirected for similar However, problems sometimes arise that the flow of the liquid enteral nutritional product is not begun because of a mechanical malfunction or distraction of the caregiver and this is not noted for a time. Sometimes the product is misdirected for similar reasons. A still further problem arises in that the nutritional product may be refluxed from the stomach or small bowel of the patient for any of various reasons of indigestion or overfeeding, and may find its way into the lungs. In such an event, special care of the patient is needed, and the problem usually becomes more serious if it is not noted fairly promptly.

In each of these instances it would ordinarily be very helpful if the presence of the liquid enteral nutritional product in an out-of-place location external to the stomach or intestines of the patient were more easily detectable. One way to more easily detect the presence of a liquid enteral nutritional product would be to make it visible by dissolving in the product a suitable physiologically acceptable marker dye. However, this may not be undertaken lightly outside of specially equipped facilities, such as a manufacturing facility, because information is usually lacking concerning compatibility of specific dyes, with various specific nutrients or medicaments that may be present in the liquid nutritional product, during heat sterilization and/or subsequent storage of the product when mixed with dye. If the marker dye is placed in solution prior to sterilization of the product there is the possibility of altering the composition of the product or the color of the dye. Moreover, the process of introduction of a marker dye, such as a food grade dye, after sterilization, may cause loss of sterility, even if certified sterile dyes are used. Thus, care must be taken to avoid contamination of a nutritional product in which organisms might multiply rapidly during storage or transport.

Drug delivery systems have been described and claimed in U.S. Pat. Nos. 4,511,353, 5,318,558 and 5,324,280 in which the drug component to be delivered is stored in a capsule from which it is ejected over time upon osmotic infusion of moisture into the capsule, the drug being carried away from the outside surface of the capsule by a suitable liquid in an intravenous, i.e., parenteral, delivery system, or even, by the device of U.S. Pat. No. 5,318,558, by body fluids upon implantation of the capsule.

In U.S. Pat. No. 5,069,671 there is described a formulation chamber, which may also be a drip chamber, in which various forms of sustained release mechanisms are employed to release a drug or medicament, or other physiologically beneficial component such as a nutrient, within the formulation chamber from which the drug or other component is carried by a suitable liquid into a parenteral delivery system.

The teachings of U.S. Pat. Nos. 4,511,353 and 5,069,671 are directed to intravenous delivery of parenteral compositions, and in the case of the latter patent, includes delivery by infusion through intravenous, intraarterial, intraperitoneal or subcutaneous routes. The osmotic dosage system of U.S. Pat. No. 5,324,280 is concerned with the delivery of drug formulations over time to a biological environment, such as a tissue or organ implant in a mammal, or a stream or tank for marine life. The osmotically driven device of U.S. Pat. No. 5,318,558 is said to be usable to deliver drugs, medicaments and nutrients in a range of environments extending from veterinary medicine to human drug administrations, and to hobby situations such as fish tanks. Again, in the case of human administration, the delivery appears to be by implantation within the tissue or an organ of the patient, followed by action of body fluids upon the osmotic device.

Although the osmotic delivery devices and other forms of sustained release dosage forms have been available for some time, so far as is known, there has been no attempt to utilize such a delivery system to add a marker dye to a liquid enteral nutritional product, with a viscosity up to 300 cps., at the time of administering the product to the gastrointestinal tract of a patient. Liquid enteral nutritional products currently on the market are described in the reference text "Nutrition In Critical Care", Gary P. Zaloga, ed., Mosby—Year Book Inc., St. Louis, Mo., 1994, at Chapter 24, authored by Barbara Hopkins, Part III, "Feeding", pp. 439–467. This reference indicates that complete nutrient compositions contain proteins, carbohydrates, fibers, fats, and vitamins and minerals, in various proportions in an aqueous or aqueous/fat medium. Nutrient compositions for special diets may omit, entirely or in part, one or more classes of these components.

SUMMARY OF THE INVENTION

A first aspect of the invention concerns an apparatus for modifying, by dye marking, a liquid enteral nutritional product during delivery from a supply thereof, such as a hangable container, to a feeding tube delivering the enteral nutritional product to the gastrointestinal tract of a patient. The apparatus comprises:

a formulation chamber connectable to a supply container of a liquid enteral nutritional product, the formulation chamber having an inlet and an outlet;

a physiologically acceptable marker dye that is soluble in the medium of the liquid enteral nutritional product, or a mixture of such dyes, the marker dye or mixture of marker dyes being contained within at least one sustained release reservoir positioned within the formulation chamber so as to be contacted by or immersed in the liquid enteral nutritional composition traversing therethrough, the amount of marker dye or mixture of marker dyes within the at least one sustained release reservoir within the formulation chamber being sufficient to visibly mark a liquid enteral nutritional product flowing through the formulation chamber during a useful period of time; and fluid communication means connecting the outlet of the formulation chamber to a tube for feeding the liquid enteral nutritional product containing the at least one marker dye into the gastrointestinal tract of a patient.

The sustained release reservoir utilized is preferably in the form of a coated capsule, osmotic delivery device, coated tablet, a microencapsulated microsphere, an agglomerate of particles of molecular sieving material, or a clump of fine, hollow, permeable-walled fibers or a coil of such a fiber, and capable of storing, i.e., retaining, and subsequently releasing a marker dye or dye mixture upon being contacted by liquid enteral nutritional product within a formulation chamber.

A drip chamber is ordinarily used here as the formulation chamber. Preferably, the sustained release reservoir(s) is shaped or held in such a manner as to prevent or avoid a sustained release reservoir blocking flow of the liquid enteral nutritional product out of the drip chamber. Also, the at least one marker dye is preferably a blue dye or a dye that fluoresces under ultra-violet light, or a mixture of the two. The color blue is not exhibited by any known body fluid.

The combination of the formulation chamber and the fluid communication means, accompanied by at least one sustained release reservoir each containing at least one marker dye that is soluble in the medium of the liquid enteral nutritional product, with the sustained release reservoir(s) disposed in the formulation chamber, or merely accompanying the formulation chamber, constitutes a useful feeding kit for feeding a liquid enteral nutritional product from a supply container into the gastrointestinal tract of a patient.

In a further aspect of the invention, the invention concerns a method of preparing a dye-marked liquid enteral nutritional product comprising modifying a liquid enteral nutritional composition during the flow thereof from a supply container containing such composition to a feeding tube leading into the gastrointestinal tract of the patient. More specifically, the method comprises the steps of:

A. providing apparatus comprising:

(a) a formulation chamber having an inlet and an outlet, the inlet being connected in fluid communication to the supply container of the liquid enteral nutritional product;

(b) a physiologically acceptable marker dye that is soluble in the medium of the liquid enteral nutritional product, or a mixture of such dyes, the marker dye or mixture of marker dyes being contained within at least one sustained release reservoir and each sustained release reservoir being positioned within the formulation chamber so as to be wetted by or immersed in the liquid enteral nutritional composition traversing therethrough, the amount of marker dye or mixture of marker dyes within the formulation chamber being sufficient to visibly mark the liquid enteral nutritional product flowing the formulation chamber during a useful period of time; and (c) fluid communication means capable of operatively connecting the outlet of the formulation chamber to the tube for feeding the dye-marked liquid enteral nutritional product into the gastrointestinal tract of the patient;

B. providing a supply container containing a liquid enteral nutritional product;

C. placing the apparatus in communicative series in the fluid flow between the supply container and the feeding tube; and, D. flowing the liquid enteral nutritional product through the apparatus where it becomes marked by the presence of the marker dye and thence into the feeding tube.

If desired, or needed, the communication means of the apparatus, which includes flexible tubing, may also include, in series, a pump to flow or promote the flow of the dye-marked liquid enteral nutritional product into the feeding tube. A peristaltic pump may be used by emplacing a portion of the flexible tubing in the pump brackets or guides to receive cam action and the pump operated during feeding. Or, the pump may be of the positive displacement type such as that described in U.S. Pat. No. 4,927,411 utilizing a disposable infusion pumping chamber cassette. Thus, the foregoing method is to be understood to include, in Step D., utilization of a pump, in addition to or in lieu of gravity flow, to promote flow of the dye-marked liquid enteral nutritional product into the feeding tube of a patient. If quick marking is desired, especially with a dye visible under normal lighting conditions, a small amount of additional marker dye not in sustained release dosage form is placed in the formulation chamber, either as a surface coating on the sustained release reservoir or separately therefrom.

BRIEF DESCRIPTION OF THE DRAWINGS

FIG. 5 is a perspective view of a drip chamber usable according to the invention with a sustained release reservoir in the form of a substantially rectangular solid disposed within the drip chamber, the beveled inlet tube end of the drip chamber being the upper end that is thrust in the normal manner through the closure of the supply container to communicate therewith and receive liquid enteral nutritional product therefrom;

FIG. 6 is a perspective view of the drip chamber of FIG. 5 inverted to show more of the detail of construction;

FIG. 16 is a perspective view of a suitable formulation chamber similar to that shown in FIG. 5, but with a different form of attachment for connection to a supply container, the screw cap here into which a supply container fits being integrally formed with the inlet end of the formulation chamber; and FIG. 17 is a perspective view of the formulation chamber shown in FIG. 16, as inverted and viewed in the opposite direction.

DETAILED DESCRIPTION OF THE INVENTION

The following terms and phrases are defined for the purposes of the description and claims.

"Liquid enteral nutritional products" refers to compositions commonly understood to be supplied in a liquid medium to and utilized in the gastrointestinal tracts of patients. Such nutritional products have a viscosity in the range of 1 to about 300 centipoises (cps.) and most frequently in the range of about 5 to about 150 cps.

"Enteral nutritional product medium" refers to the liquid portion of a liquid enteral nutritional product, mainly water, but often including lesser or minor amounts of one or more non-aqueous substances such as lipids, e.g., a vegetable oil or marine oil.

The term "gastrointestinal tract" as used herein refers only to the stomach and the small bowel. Feeding to the gastrointestinal tract is done by use of a nasogastric tube extending through a nasal passage and the esophagus and thence to the stomach, or by use of a feeding tube extending through the abdominal wall to the stomach or small intestine.

The term "feeding set" refers to the combination of a formulation chamber loaded with one or more sustained release reservoirs containing, in total, at least a sufficient amount of physiologically acceptable marker dye or dye mixture to color under normal lighting conditions or make visible under ultraviolet light a substantial amount of liquid enteral nutritional product over time, and, fluid communication means connectable to a feeding tube for enteral feeding.

By the phrase "to visibly mark the liquid enteral nutritional product" means to mark visibly to a sufficient extent under either visible or ultraviolet light so that the presence of dye in the nutritional product is evident to the human eye. Visible light is sometimes referred to as white light.

The term "delivery means" denotes generically a means or system for storing and subsequently delivering within a formulation chamber, such as a drip chamber, a physiologically acceptable marker dye that is soluble in the medium of the liquid enteral nutritional product transiting the formulation chamber.

The sustained release reservoirs are to be understood to also be "rate controlling means" or "rate controlled dosage forms" or "sustained release dosage forms".

Figure 1:
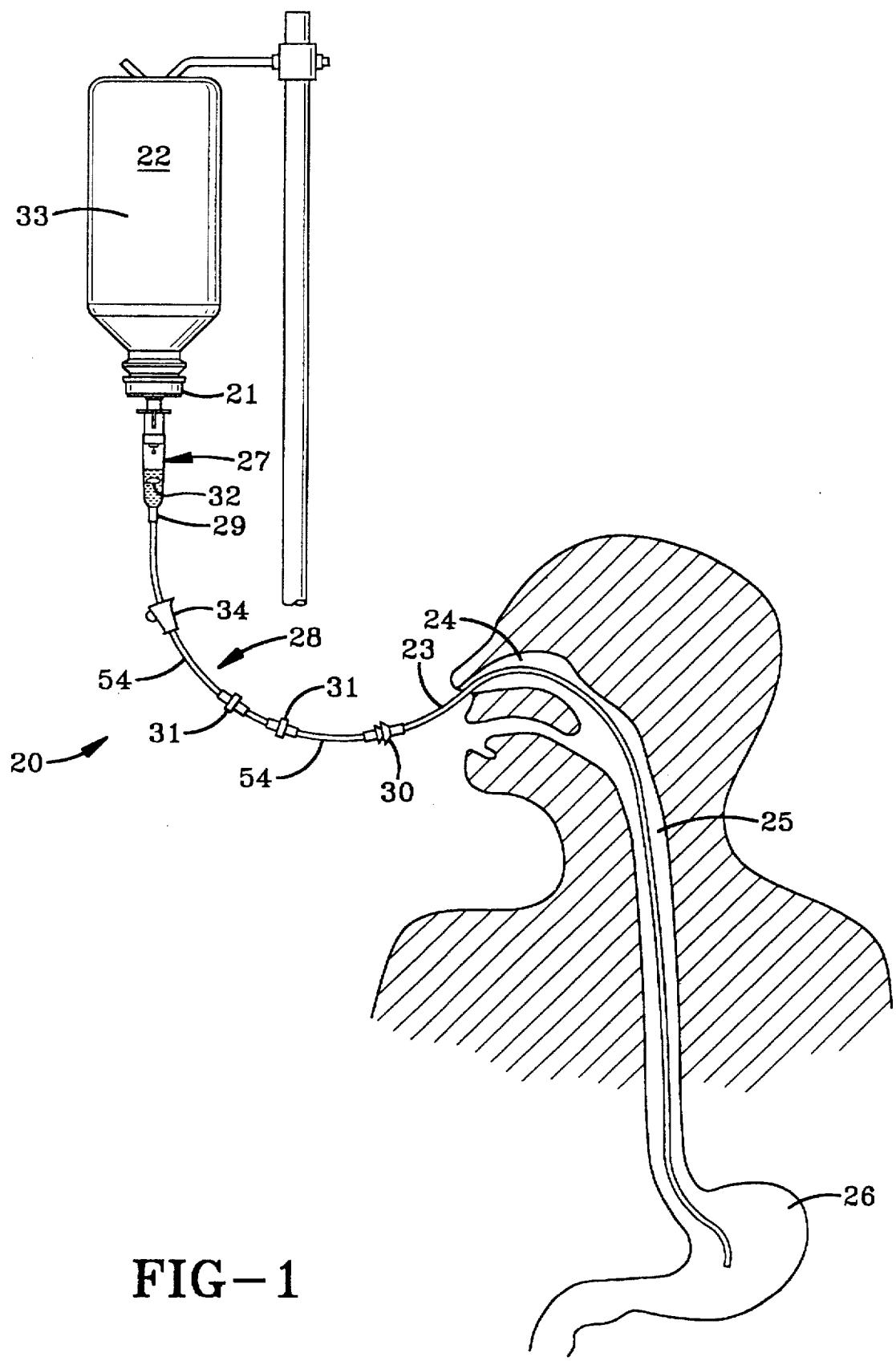
FIG. 1 is a partly schematic representation of an apparatus for dye-marking a liquid enteral nutritional product and tube feeding it nasogastrically, the apparatus including a feeding set in which the nutritional product is dye marked according to the invention while the nutritional product is being conducted from a hanging container to a nasogastric feeding tube.

Referring now to the drawings in which like parts are referred to by like reference numerals, the apparatus of the invention is shown in FIG. 1 in the form of a feeding set, indicated generally by the numeral 20, connecting the outlet 21 of the hanging supply container 22 to the nasogastric feeding tube 23 that extends through a nasal passage 24 of the patient and down the esophagus 25 to the stomach 26. The feeding set here consists of a drip chamber 27, that serves also as a formulation chamber for the uptake of the marker dye or dyes into the liquid enteral nutritional product 33 flowing from the supply container 22, and fluid communication means indicated generally by the numeral 28. The fluid communication means consists in large part of one or more pieces of flexible tubing 54, usually of a clear plastic such as a polyvinylchloride. If there is more than one piece of tubing they are connected in series or used to connect other components in series by means of connector elements 31.

Each formulation chamber selected for use, as well as the sustained release reservoir or reservoirs used therein during a given feeding, is shaped and/or positioned, usually the sustained release reservoir relative to the chamber, so that the sustained release reservoir(s) will be contacted or wetted by or immersed in the liquid enteral nutritional product flowing through the chamber. Preferably the drip chamber is used as a formulation chamber, though a formulation chamber may or may not be used in addition to a drip chamber, and a formulation chamber does not have to be, or have to serve as, a drip chamber when used in series with a drip chamber. A drip chamber is almost always employed so that the flow of liquid enteral nutritional product from the supply container may be monitored visibly, so it may as well be used as the formulation chamber as well.

Figure 4:
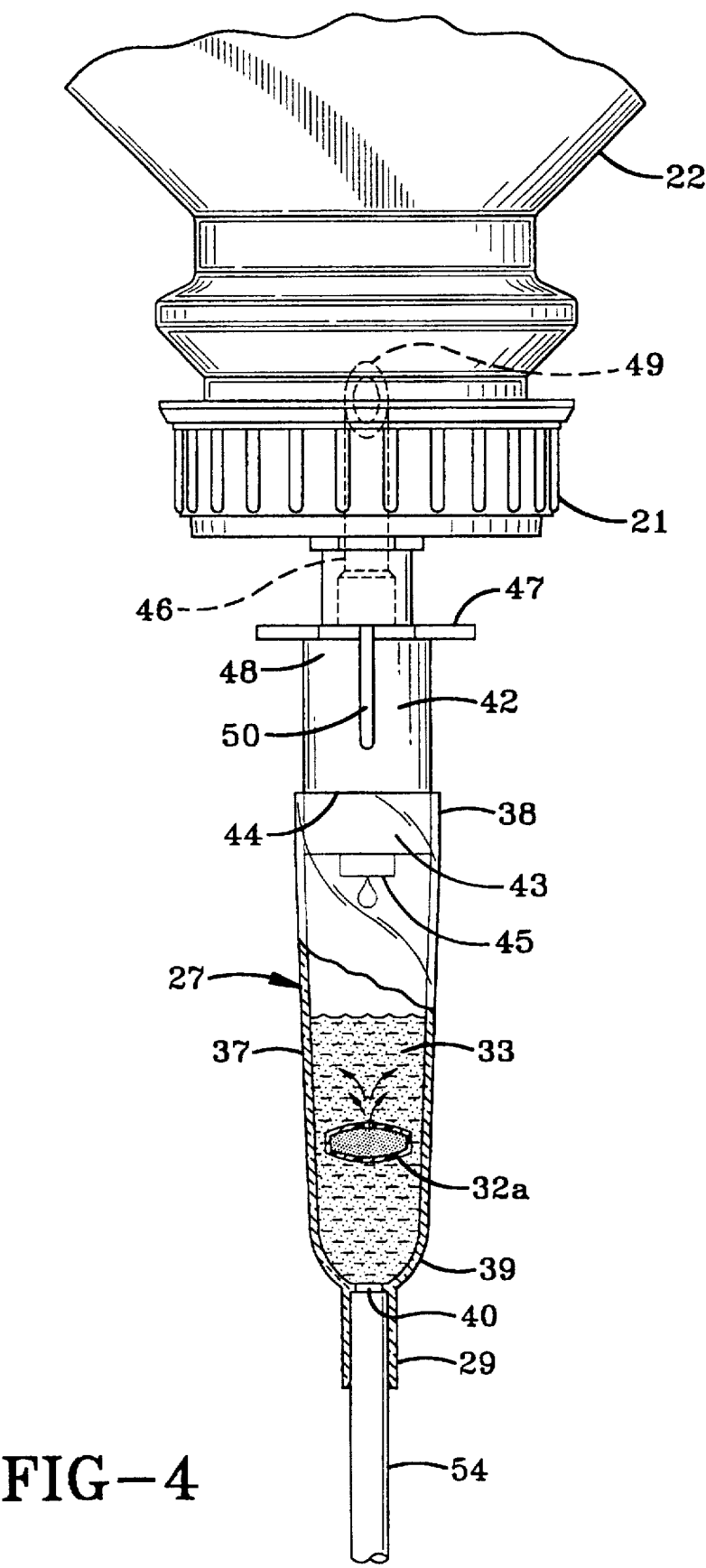
FIG. 4 is an enlarged fragmentary view in front elevation of the lower portion of a hanging supply container of a liquid enteral nutritional product, such as the supply container shown in FIGS. 1 to 3, with the beveled end of the inlet tube of a drip chamber inserted through the container closure and the drip chamber depending therefrom and with a sustained release reservoir disposed inside the drip chamber and immersed in the flowing liquid enteral nutritional product, the lower part of the drip chamber and the sustained release reservoir within being partly broken away and in section, and the fluid communication means, i.e., here primarily the flexible tubing leading away from the drip chamber, being truncated for purposes of illustration.

A "formulation chamber" is a hollow, flow-through chamber, column-like in most instances, in which one or more sustained release reservoirs are positioned. Examples of a variety of suitable formulation chamber designs for use in addition to a drip chamber, or where a drip chamber is not needed, are shown in FIGS. 4 and 5 of U.S. Pat. No. 5,069,671. Formulation chambers of other designs may be needed or useful, such as that shown herein in FIG. 15, for use in a horizontal position, and, a formulation chamber with a different attachment to the supply container as depicted in FIGS. 16 and 17.

"Fluid communication means" is to be understood to include all components of fluid communication utilized, ordinarily in series, from the drip chamber outlet 29 to the flexible tubing 54 to the connection 30 to the feeding tube, such as the nasogastric feeding tube 23. Components include not only the flexible tubing 54 and any segments of the tubing, if any, but also any additional specially adapted or shaped tubing portions and/or connectors, if needed, for utilization of a pump to aid the flow of the nutritional product to the patient, such as the pump 35 shown schematically in FIG. 3. Connector elements, or adapters 31, may be used between pieces of tubing 54 connecting other components.

The drip chamber 27 is loaded with a sustained release reservoir 32 containing at least a sufficient amount of a physiologically acceptable marker dye or mixture of marker dyes to impart visibility, under appropriate lighting conditions, to a liquid enteral nutritional product 33 flowing from the supply container 22 into the drip chamber 27 where the nutritional product, which is usually water-based, contacts the sustained release reservoir 32, or a plurality thereof, wetting it or immersing it in the flow, causing the release or discharge into the nutritional product of the marker dye or dyes stored in the reservoir.

A "marker dye or dye mixture" that is useful according to the invention is a colorant dye or a fluorescent dye or a mixture of such dyes that is physiologically acceptable to the patient and is capable of being taken up in detectable concentration in the liquid medium of the liquid enteral nutritional product while the product flows through a formulation chamber, such as a drip chamber, having positioned therein at least one sustained release reservoir containing the marker dye or dyes.

The marker dye employed may be a colorant dye that imparts color that is visible under white light, i.e., under normal daylight or artificial room light encountered in a hospital or clinic, or, the marker dye may be a fluorescing dye, such as, F.D.& C. Red #3 dye, that fluoresces visibly under ultraviolet light, or a mixture of a colorant dye and a fluorescing dye. A mixture of a colorant dye and a fluorescing dye appears to be especially advantageous in that flow through the drip chamber is readily perceived under normal lighting conditions with colorant dye present, while even a small amount of nutritional product out of place, for example, in the oral cavity or a nasal passage, will be more easily detected with the aid of ultraviolet light if it contains a fluorescing dye. This is because of the nature of the fluorescing dyes in that they are especially visible under ultraviolet light even when present in very low concentration.

It is essential that the dye or dye mixture be soluble in the liquid medium of the liquid enteral nutritional product. Generally, food grade dyes may be used where a colorant dye is desired. F.D.& C. Blue #2 blue dye is a preferred dye, while F.D.& C. Blue #1 dye is even more preferred for color marking the liquid enteral nutritional products. F.D. & C. here refers to the so-called "Food, Drug and Cosmetic Act" of the United Sates of America, and dyes approved for food use under its provisions are identified in the above manner.

F.D.& C. Red #3 red dye is a preferred fluorescing dye.

A "useful amount" of a physiologically acceptable marker dye or mixture of such dyes is an amount sufficient to mark visibly to the human eye, either by color under white light or by fluorescence under ultraviolet light, a liquid enteral nutritional product over time for a preselected period in the range of from about 1 minute to 30 hours or more, but generally at least 2 hours and not more than 24 hours, in accord with typical feeding practices which is usually a process of infusion.

The process of "infusion" is meant to refer, in the present context, to the process of supplying a liquid enteral nutritional product containing a marker dye over time, such as from at least one minute and up to 48 hours, generally not more than 24 hours, but preferably for at least as long as the liquid enteral nutritional product is being fed and microbiologically safe, e.g., when feeding from a given feeding set connected to a supply container containing a low-acid nutritional product. Such feedings generally continue for at least two hours and may continue for longer periods up to about 24 hours, but may be carried out intermittently, rather than continuously.

The sustained release reservoirs used according to this invention contain only marker dye or a mixture of such dyes, apart from any excipients, such as mannitol, sorbitol, sodium or potassium alginate, sodium carboxymethylcellulose, hydroxypropylmethylcellulose, hydroxypropylcellulose, potassium or sodium chloride, polyvinylpyrrolidone, triethyl citrate, cellulose acetate, magnesium stearate or polyethylene oxide that may be employed in minor amounts of up to about 10 percent by weight of the dye present to moderate solubility of the dye or dyes in the medium of the liquid enteral nutritional product.

The term "sustained release reservoir" for the purposes of the specification and claims is meant to refer to a coated tablet, osmotic release device, coated capsule, microspheres that have been microencapsulated, agglomerated molecular sieving particles, or, permeable-wall, fine hollow fibers that have been coiled or chopped and placed in a porous carrier, in which marker dye is stored prior to use according to the present invention and released in a sustained manner during a feeding period when immersed in or otherwise contacted in a formulation chamber, such as a drip chamber, by a flowing stream of a liquid enteral nutritional product.

In the case of the osmotic devices, which are preferred sustained release reservoirs because of steadier, more predictable, delivery of the dye into the flowing liquid enteral nutritional product for many hours at a moderately sustained rate, the sustained release reservoir is provided with an external coating or membrane that maintains its integrity during delivery of the dye. The osmotic delivery types of sustained release reservoirs can be designed for various capacities or feeding times so as to not fall off in rate of release to less than about 25% of the initial rate until the reservoir is nearly exhausted. The other types of sustained release reservoirs are usually less costly but tend to release the dye at a rate that varies even more with time, which may be overcome to some extent, for example, with the microencapsulated microspheres reservoirs mixtures that contain microsphere particles of the dye being coated with a range of coating thicknesses from none to about six coats that dissolve or become permeable at successive intervals. The molecular sieving types have a non-linear release curve for each grade or type of sieve. Mixtures of sieve grades may be used to flatten the curve. So long as the marker dye is released persistently in sufficient amount over a feeding period to serve as a marker, these other non-osmotic types of sustained release reservoirs appear to be adequate. With more variable or greatly changing release rate of marker dye, the depth of color or fluorescence, however, cannot be used to gauge the extent of dilution of the nutritional product, should it be diluted by body fluids.

Referring again to FIG. 1, the flow of nutritional product is conveniently started or shut off or sometimes merely regulated by the use of a conventional adjustable compression clip 34 through which the flexible tubing 54 extends, though regulation tends to be difficult using just the clip.

Figure 2:
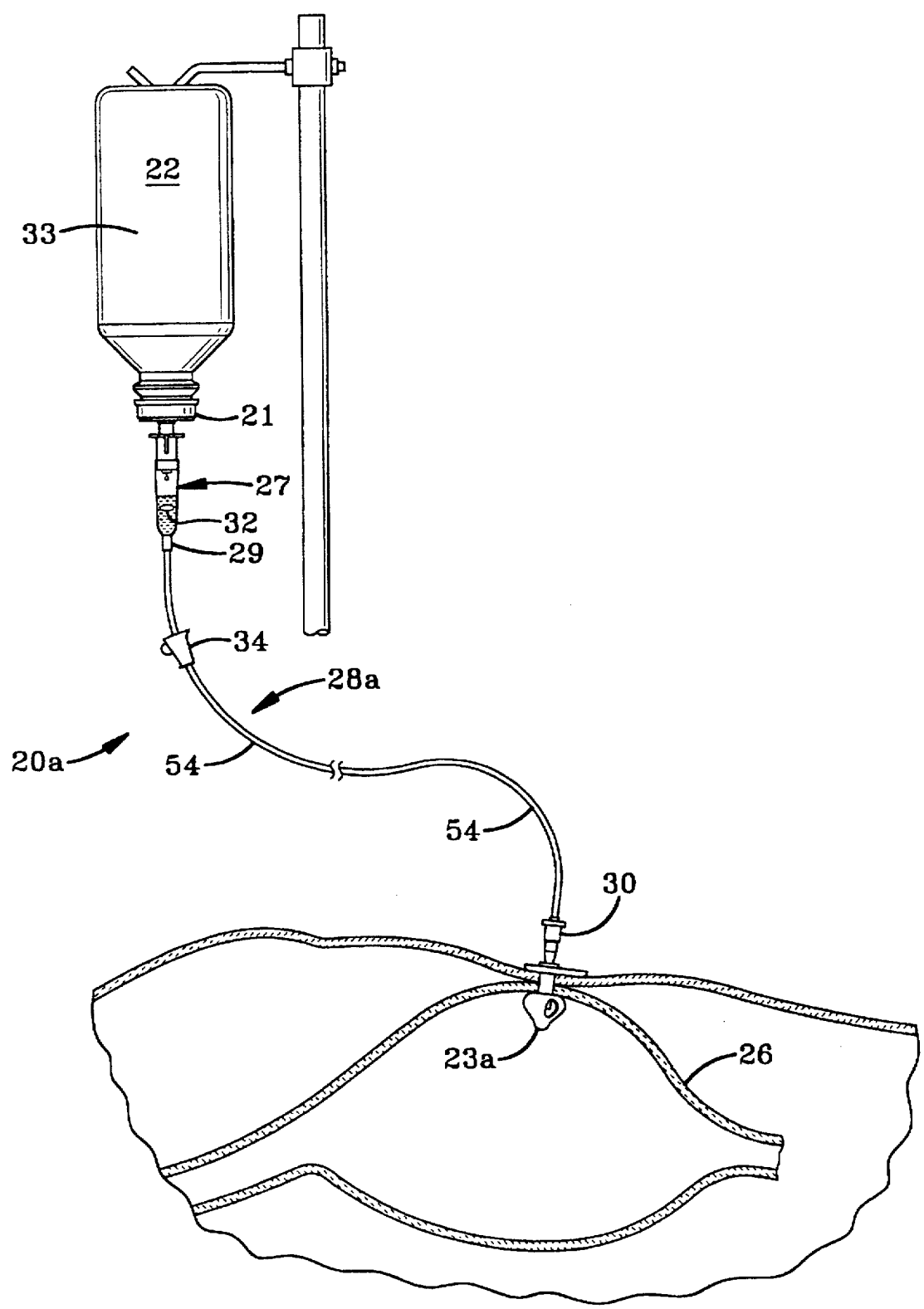
FIG. 2 is a partly schematic representation of an apparatus for dye-marking, according to the invention, a liquid enteral nutritional product and tube feeding it via a gastrostomy tube.

Turning now to FIG. 2, a hanging supply container 22 is shown supplying liquid enteral nutritional product 33 to a drip chamber 27, which functions as a formulation chamber, from which the nutritional product flows to the feeding set 20a and to the gastrostomy feeding tube 23a. The gastrostomy tube 30 shown in FIG. 2 is merely exemplary of the numerous varieties of gastrostomy feeding tubes that are commercially available, and it is to be understood that the present invention may be used in conjunction with any such gastrostomy feeding tube.

Figure 3:
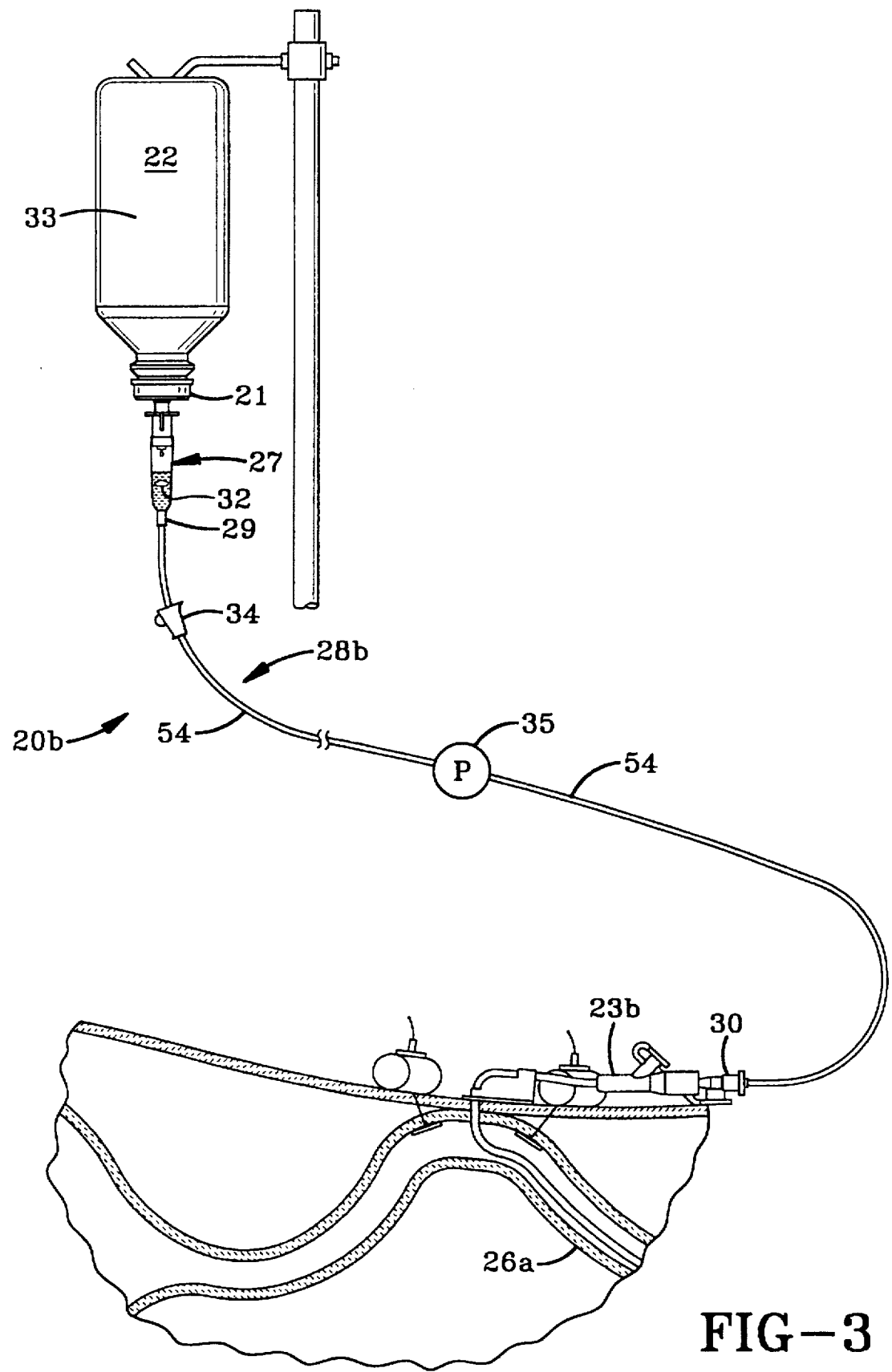
FIG. 3 is a partly schematic representation of an apparatus for dye-marking, according to the invention, a liquid enteral nutritional product and tube feeding it, with the aid of a pump, via a jejunostomy tube.

In FIG. 3 there is shown a feeding arrangement for a jejunostomy much like the apparatus depicted in FIG. 1, except that after the enteral nutritional product medium-soluble marker dye has been added to the liquid enteral nutritional product 33 flowing from the hanging supply container 22 to the sustained release reservoir in the drip chamber 27 serving as a formulation chamber, the dye-marked composition moves through the feeding set 20b to the jejunostomy feeding tube 23b. Feeding set 20b is shown being used with a pump 35, which provides positive flow into the small bowel or jejunum 26a of the patient, for which gravity flow is less often utilized unaided. In any feeding set in which a pump is utilized in series as here, the pump 35 may be a peristaltic pump with cam action acting upon a section of the flexible tube portion of the communication means, in some cases with a specially shaped tubing portion to fit the pump housing. The pump 35 may also be a positive displacement pump with a disposable fluid infusion pumping chamber cassette such as that described in U.S. Pat. No. 4,927,411. A pump may be used in any appropriate type of tube feeding procedure, for example, when it is not convenient to hang or otherwise locate the supply container in an elevated position relative to the patient, or, when the nutritional product is rather viscous and flows slowly by gravity flow.

In the enlarged fragmentary view in FIG. 4 a sustained release reservoir 32a in the form of an osmotic pump device is seen immersed in liquid enteral nutritional product 33 within the drip chamber 27 which functions as a formulation chamber. This type of sustained release reservoir which has an external envelope or membrane that maintains its integrity should have a geometric solid or other non-spherical shape that will prevent or avoid totally blocking the flow of liquid enteral nutritional product 33 through the outlet of the drip chamber 27, or other means may be employed to prevent such blockage. Suitable geometric solid shapes usable with a drip chamber, or other formulation chamber, that is round in section include: a polyhedron, such as a rectangular solid, a tetrahedron or a pentahedron. The sustained release reservoirs may be designed with corners rounded slightly to avoid damage occurring readily on handling, but pointed shapes, such as star shapes, are also usable.

The details of construction of one example of a conventional drip chamber which may be employed as a formulation chamber are illustrated in FIGS. 5 and 6, which are greatly enlarged perspective views taken in respective opposed directions. Such a drip chamber, in this case, serves also as a formulation chamber and serves in that capacity in the apparatus depicted. The drip chamber 27 as shown has two parts. The first part is a hollow, nearly cylindrical, or slightly tapered, chamber body 37 of greater than about 5 milliliters (ml.), and up to about 250 ml. capacity, but more generally from about 10 ml. to about 25 ml., capacity, with an open first end 38 and a second end 39 that narrows down to form an outlet orifice 40 leading to an integrally formed outlet tube portion 29. When a drip chamber is in its normal operating position it is upright or nearly so, with the first end 38 disposed higher than the second end 39. The chamber body 37 must be formed of a clear, see-through material, such as plastic or glass, to allow visibility of the flow of the nutritional composition. Usually the drip chamber is formed of a clear, somewhat flexible, autoclaveable plastic, such as a clear polyvinylchloride or polyolefin resin.

The second part of this first exemplary drip chamber 27 is in the nature of a plug 42 with a cylindrical body that has an inward end portion 43 that snugly press fits into the first end 38 of the chamber body 37. Preferably the inward end portion 43 of the plug body 42 has a slightly reduced diameter, the proximate edge 44, i.e., the edge toward the beveled end 49 of the inlet tube 46, of which serves as a stop when assembling the two parts. The plug body is provided with an integrally formed fluid communication passage 45 which may take the form of an axial borehole in a solid plug body that communicates with the inlet tube portion 46 that projects outwardly in the axial direction from a collar-like flange 47 that extends radially from the top end 48 of the plug body. But, preferably, in order to provide a plug body with more resiliency for easier insertion into the first end 38 of the chamber body 37, the fluid communication passage 45 is a concentric tube axially located within and about as long as the plug body, which in this case is mainly a hollow cylinder, except for a short solid middle portion. The concentric tube 45 is integrally formed with or otherwise connected in fluid communication with the inlet tube portion 46. A short, peripheral, integrally formed flange 50 that extends longitudinally from the collar-like flange 47 along a side of the plug body may be provided, if desired, to aid in gripping the plug body when assembling the drip chamber. The plug body may be molded of a plastic such as polyvinyl chloride resin and may be pigmented, if desired.

The distal, i.e., free, end 49 of the inlet tube portion 46 has a sufficiently sharp beveled end to facilitate puncturing the seal (not shown) in the closure of the conventional hanging supply container, such as supply container 22. The collar-like flange 47 serves as a stop to the insertion of the pointed or beveled inlet tube portion 46 into the closure in any of the conventional connecting means provided at the neck of the supply container 22.

A second exemplary construction of a drip chamber that will function suitably as a formulation chamber in the apparatus used in the present invention is shown in FIGS. 16 and 17. The drip chamber 82 illustrated in these views has a plug end 83 that is integrally formed with the closure 84 for one of the conventional styles of supply container (not shown) to which the drip chamber 82 is readily threadably connected and from which it is hung.

Other modes of construction of the drip chamber may be employed so long as a suitable connection to the supply container is provided as well as a see-through tubular chamber portion wherein the rate of drip or flow of the liquid enteral nutritional product may be observed.

Figure 15:
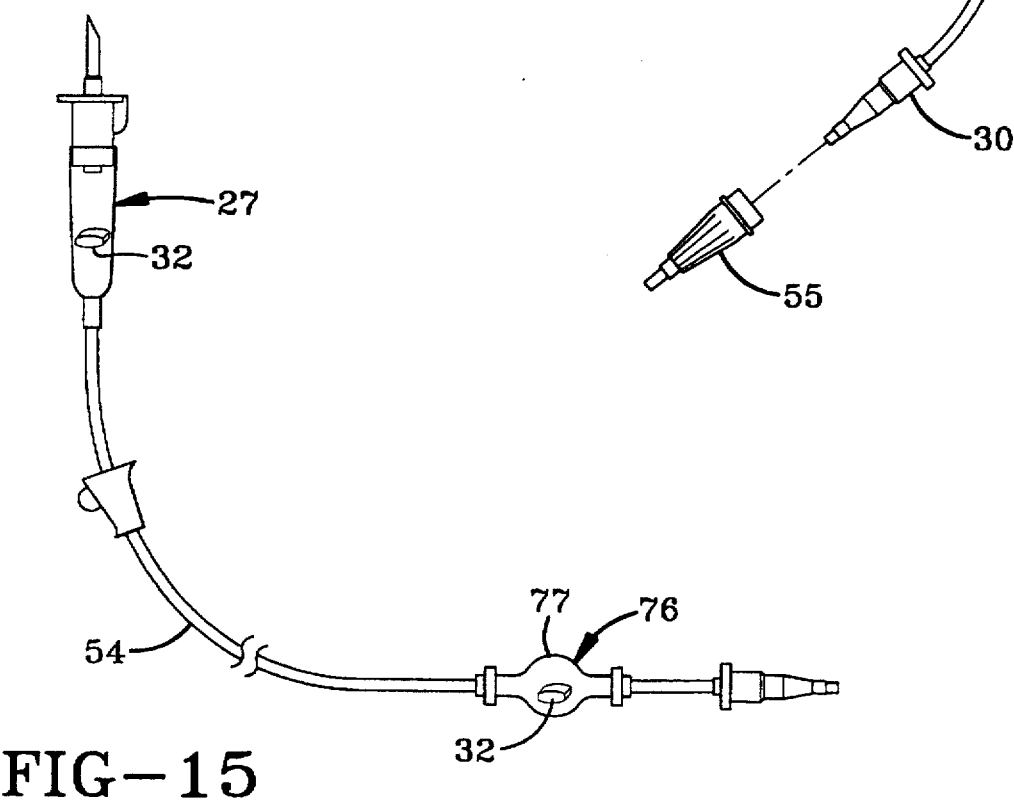
FIG. 15 is a view in side elevation of a feeding kit in which a second formulation chamber has been attached by its inlet in fluid communication to the connector at the end of the flexible tubing that normally attaches to a fitting that connects to the feeding tube of the patient, the outlet tube of the second formulation chamber having a fitting for connection to the feeding tube.

The apparatus of the invention is not to be considered limited to the inclusion of the drip chamber here shown by way of illustration, nor is the method limited to the use thereof. For example, the formulation chamber 76 shown in FIG. 15 is suited for use in a horizontal position at the end of flexible tubing 54 of a feeding set which is distal from the supply container and at about the level of the bed of a patient. The caregiver may find it more convenient to attach such a formulation chamber 76 at the end of the flexible tubing 54 which is distal from the supply container rather than take the feeding set apart adjacent the drip chamber, particularly if there is a need or desire to introduce a fluorescing marker dye into the nutritional product, by the use of a sustained release reservoir during feeding, in addition to a colorant dye that is in a sustained release reservoir in the drip chamber 27. The formulation chamber shown has provision to so hold or support one or a plurality of sustained release reservoirs so that liquid enteral nutritional product being fed will be guided onto and over the sustained release reservoir(s). In this embodiment, the formulation chamber has a bulbous mid-section 77 in which the sustained release reservoir 32 is placed so that the flowing stream of nutritional product 33 will flow over it and take up marker dye from the reservoir. The formulation chamber may also be shaped or molded with a longitudinal groove along the sidewall of the lower side of the chamber body and the sustained release reservoir(s) placed in such groove before beginning feeding.

In all embodiments of the present invention the formulation chamber is a hollow, flow-through chamber having an inlet and an outlet and is suitable for receiving therewithin at least one sustained release reservoir in a position in which the sustained release reservoir or reservoirs will be contacted by liquid enteral nutritional product flowing through the formulation chamber while the formulation chamber itself is supported or held in its normal intended orientation.

The drip chambers shown in FIGS. 5, 6, 16 and 17 have a sustained release reservoir 32 disposed therein ready for use. The sustained release reservoir contains at least one acceptable marker dye in accordance with the objectives of the invention. More than one sustained release reservoir may be placed in the drip chamber if needed to provide sufficient depth of color, or fluorescence, as the case may be, or to provide a longer period of dye marking. Thus, the reservoirs may be selected to have different release rates or one of the reservoirs may provide a delayed onset of release to extend over a longer period of time.

The sustained release reservoir will usually be in the form of a coated tablet, osmotically driven device, coated capsule, microencapsulated microsphere, agglomerated molecular sieving particles or permeable-wall hollow fiber pieces within a porous carrier or envelope or as a fiber coil, holding a given amount of dye or an amount providing a given time period of marking. To avoid having the sustained release reservoir 32 substantially block the flow of the liquid enteral nutritional product through the outlet orifice 40 of the drip chamber 27 or other formulation chamber, it is preferred that the individual reservoirs or carrier of a plurality thereof, and, the outlet 40, have mutually non-complementary shapes to facilitate flow of liquid therebetween. For example, the sustained release reservoir may be shaped substantially as a rectangular solid or as a pointed, star-shaped solid, which will not block a cylindrical or tapered cylindrical chamber that necks down to a round orifice to the outlet passageway 29. This is particularly pertinent if the sustained release reservoir is one that maintains integrity of the exterior layer or coating thereof or the carrier therefor while the ingredients leach out or are expressed out during contact with the liquid enteral nutritional composition.

Figure 11:
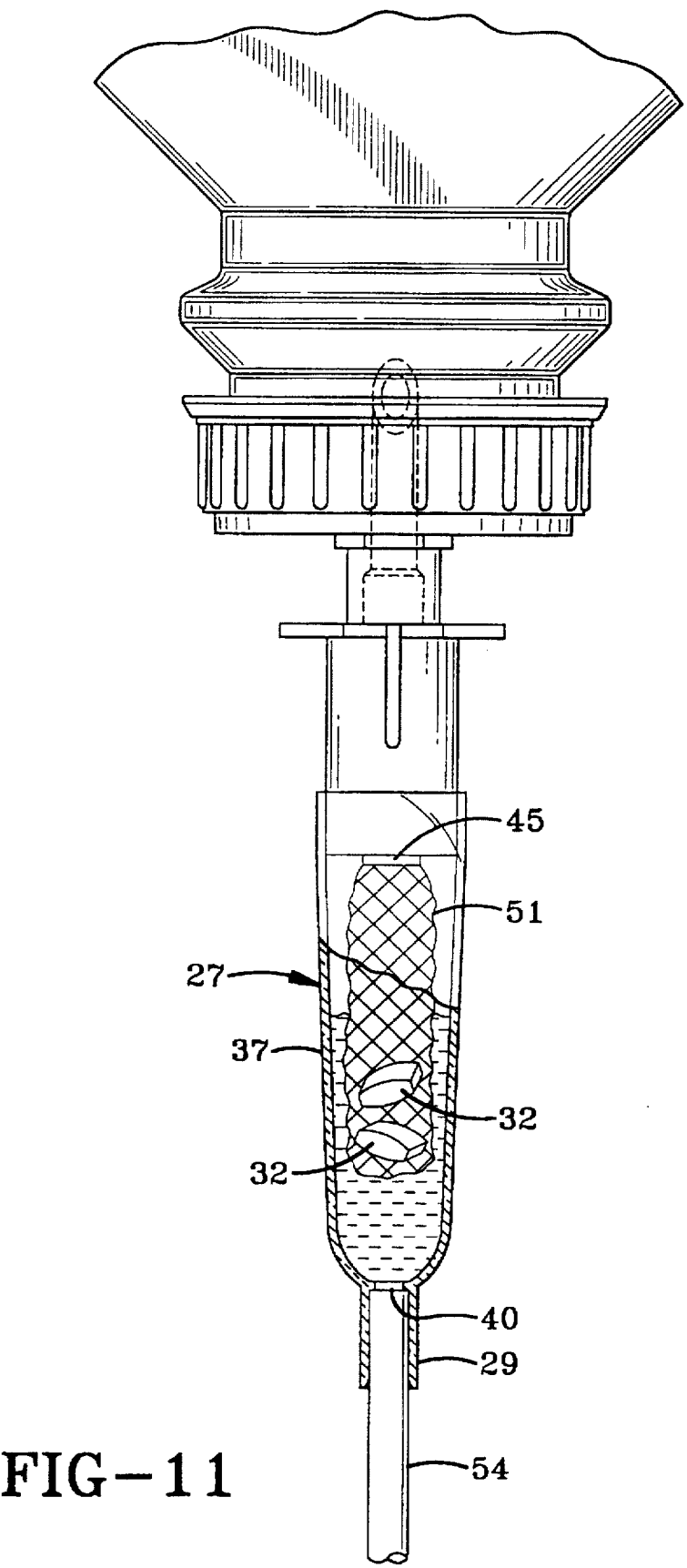
FIG. 11 is a view similar to FIG. 4, but with the sustained release reservoir of any of FIGS. 7 to 9A confined within a mesh sleeve or bag.

If a different type of sustained release reservoir is used that does not maintain integrity of its coating or envelope or carrier it is preferred to dispose the sustained release reservoir in some kind of confinement such as the mesh bag 51 shown hung from the inner end of the inlet tube 45 within the drip chamber in FIG. 11. With this kind of sustained release reservoir there is little need for special shapes of the reservoirs as the confinement means used can prevent the plugging of the outlet orifice 40 of the drip chamber. In FIG. 11 there is also shown a plurality of sustained release reservoirs 32 as may be employed in order to provide additional dye to obtain greater depth of dye marking, if desired.

Figure 12:
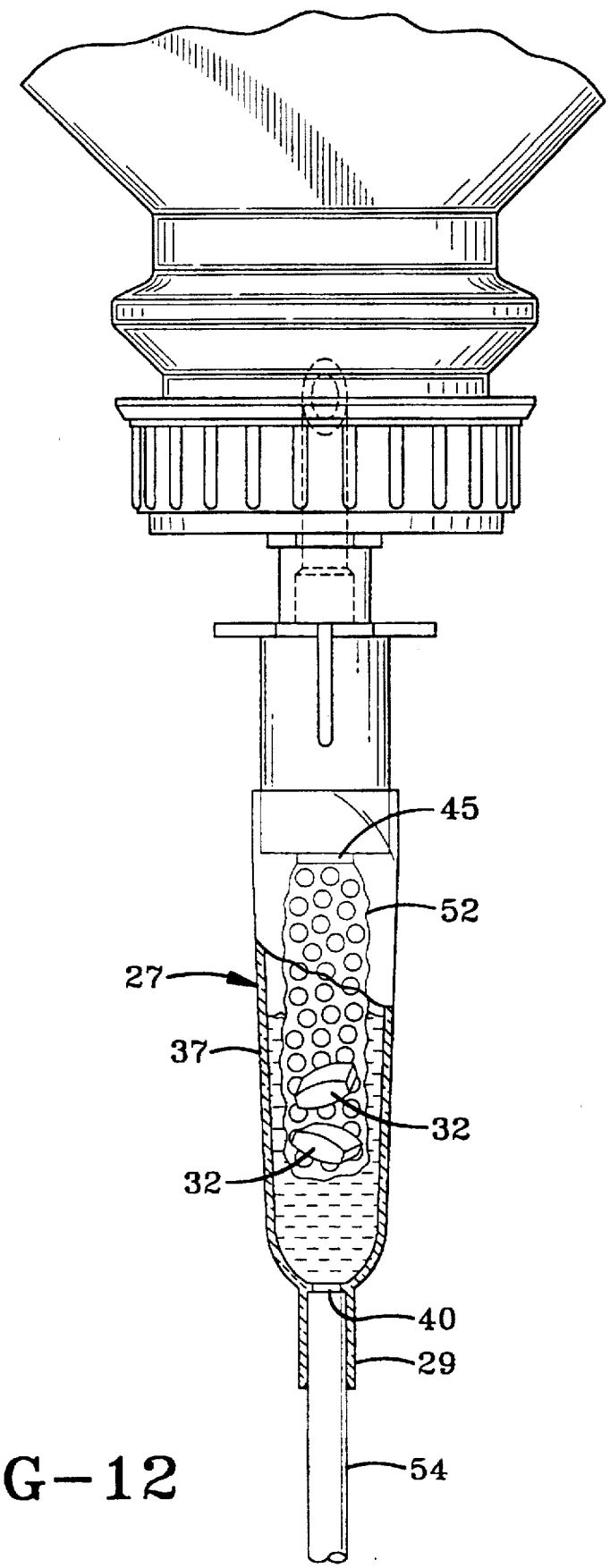
FIG. 12 is a view similar to FIG. 4, but with the sustained release reservoir of any of FIGS. 7 to 9A confined within a foraminated, or pierced, sleeve or bag.
Figures 13, 13A:
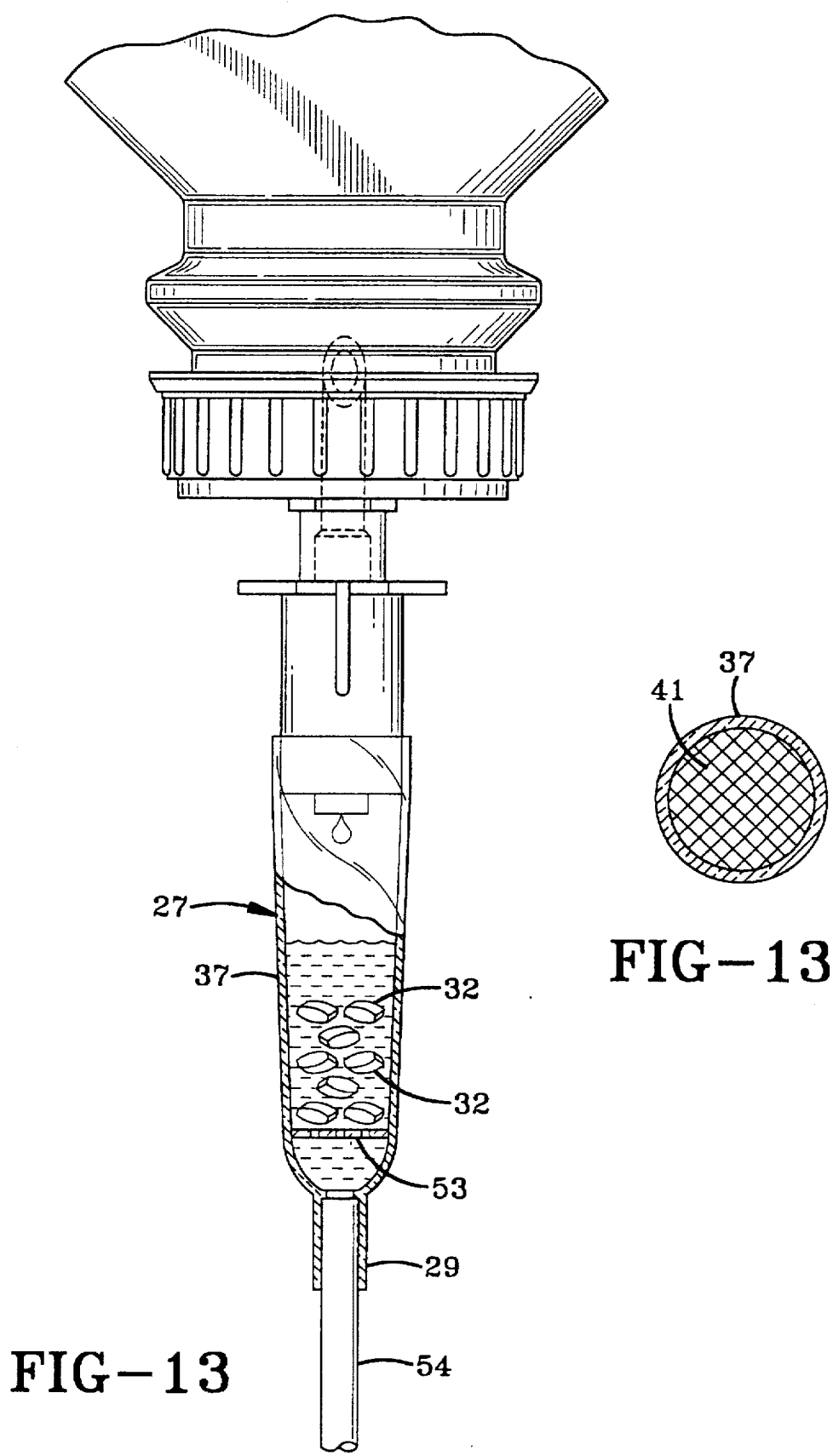
FIG. 13 is a view similar to FIG. 4, but with a plurality of the sustained release reservoirs or carriers of FIGS. 7 to 9A supported by a foraminous plate above the outlet orifice of the drip chamber.
FIG. 13A is a view in transverse section of a formulation chamber taken at the level just above a grid that may be used in place of the foraminous plate in the drip chamber shown in FIG. 13.

As seen is FIG. 12, a foraminous sleeve-like bag, that is, one with numerous holes in it, may be hung within the drip chamber and used to position and confine the sustained release reservoir(s) in the drip chamber. Or, as seen in FIG. 13, a plastic or ceramic or inert metal plate 53 that is foraminous or pierced may be placed transversely across the lower part of the drip chamber body 37 to support the sustained release reservoir(s). In FIG. 13 there is shown a very large number of sustained release reservoirs 32 used to obtain long term dye marking release from tablets or capsules that each release dye very slowly, or, depending on release rates, to obtain a greater concentration of marker dye in the nutritional product.

In FIG. 13A there is shown a transverse section of the body 37 of the formulation chamber taken just above a grid 41, of ceramic or plastic material or an inert metal like stainless steel, that may be used in place of the foraminous plate 53 in the drip chamber 27 of FIG. 13 to support one or more sustained release reservoirs.

Figure 7:
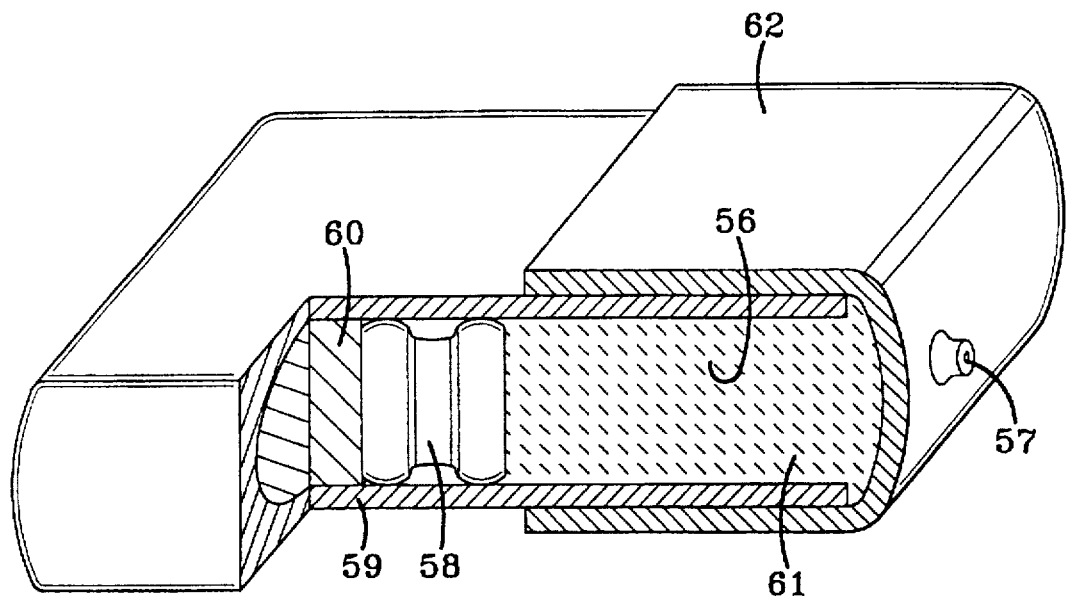
FIG. 7 is a perspective view, partly broken away and in section, of a rectangular solid-shaped sustained release reservoir, of the osmotic pump type, used to supply a physiologically acceptable marker dye within the drip chamber according to the invention, the dye being in liquid form in the reservoir and soluble in the medium of the liquid enteral nutritional product.

The sustained release reservoir depicted in FIG. 7 is of the osmotic pump type that functions in the manner of the osmotically driven delivery device described and claimed in U.S. Pat. No. 5,318,558, the specification and drawings of which are incorporated herein by reference with respect to the structure of the sustained release reservoirs there described and the method of making them and their mode of release, albeit here with different environments and contents and end uses. The pump type reservoir comprises (a) a first body wall portion 59 defining an enclosed elongated cavity that is essentially cylindrical with first and second ends, (b) a piston 58 longitudinally slideable in the cavity while slidably touching the surrounding first body wall portion 59, and (c) an orifice 57 formed therethrough a second body wall portion 62 at the second end of the cavity. The piston defines first and second zones within the cavity. The first zone 60 is filled with a hydro-active substance, while the second zone 61 is filled with a marker dye in liquid or solution form. The body wall portions 59 and 62 together provide a complete closure. The first body wall portion 59 surrounds the first zone and first end of the cavity and a portion of the adjacent second zone and is formed of a moisture permeable membrane. The second body wall portion 62 surrounds the second end of the cavity and telescopically overlaps a part of the first body wall portion 59 and is formed of a membrane that is non-permeable to the medium of the liquid enteral nutritional product. It is through the second body wall 62 portion at the second end of the cavity that an orifice 57 is formed for the discharge of marker dye into flowing liquid enteral nutritional product. Each of the body wall portions is of a material that maintains its integrity for at least 24 hours in the presence of moisture.

In the pump type reservoirs the ingredient to be fed, such as the marker dye or dye mixture here, in liquid or solution form, is expressed out from the cylindrical enclosure or cavity 56 within the reservoir through a very small orifice 57 by the action of a piston 58 driven by pressure developed by osmotic infusion of moisture, taken in from a liquid enteral nutritional product, through a semi-permeable membrane 59 confining a hydro-active substance 60 behind the piston 58, driving the piston steadily toward the side of the reservoir where the dye or dye mixture 61 is forced out gradually through the orifice 57. The enclosure 56 is formed within a non-permeable membrane or coating 62.

Figure 8:
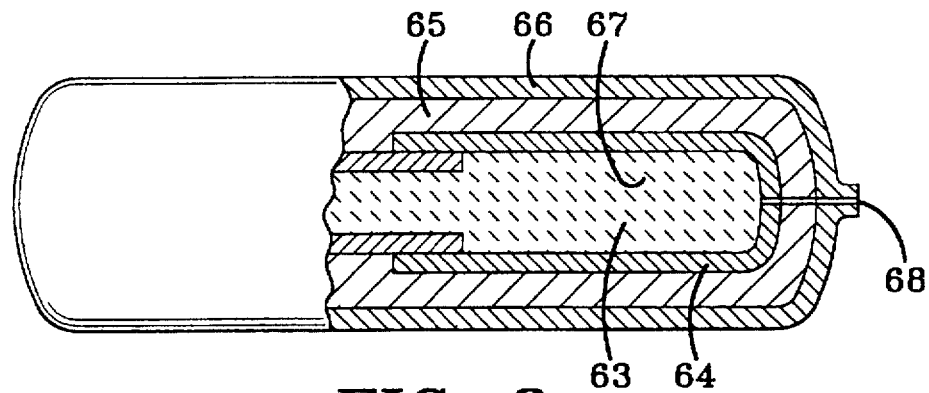
FIG. 8 is a view in front elevation, partly broken away and in section, of a rectangular solid-shaped sustained release reservoir, of another osmotic device type, used to supply at least one physiologically acceptable marker dye within the drip chamber according to the invention.

The sustained release reservoir depicted in FIG. 8 is another osmotic dosage system with a sustained release reservoir that functions in the manner of the osmotically operated delivery device described and claimed in U.S. Pat. No. 5,324,280, the specification and drawings of which are hereby incorporated herein by reference with respect to the structure of the sustained release reservoirs there described and the method of making them and their mode of release, albeit here with different environments and contents and end uses. This type of osmotic device comprises (a) a capsule formed by an exterior wall made up, at least in part, by a semi-permeable composition that maintains its integrity in the presence of an aqueous fluid, (b) a hydro-activated layer surrounded by the exterior wall and comprising a hydro-activated swellable composition or a hydro-activated composition that occupies space at a controlled rate, (c) an inner capsule surrounded by the hydro-activated layer, and (d) a lumen communicating with the inner capsule and extending to the exterior of the outer capsule. The inner capsule contains at least a useful amount of water soluble marker dye in liquid or solution form. The wall of the inner capsule is substantially non-permeable to the liquid enteral nutritional product being fed.

In this type of system, the ingredient, such as the dye or dye mixture 63 here, to be fed in liquid or solution form, is enclosed within a non-permeable coating 64 that is surrounded by a layer 65 of hydro-active material that is entirely confined within an outer membrane coating 66 that is semi-permeable to the liquid medium of a liquid enteral nutritional product. Osmotic pressure developing in the hydro-active layer 65 upon infusion of moisture thereinto from the liquid enteral nutritional product compresses the core 67 containing the liquid dye or dye mixture 63 and forces that liquid out steadily over time through a very small passageway 68 from the core 67 to the exterior of the reservoir.

Figure 8A:
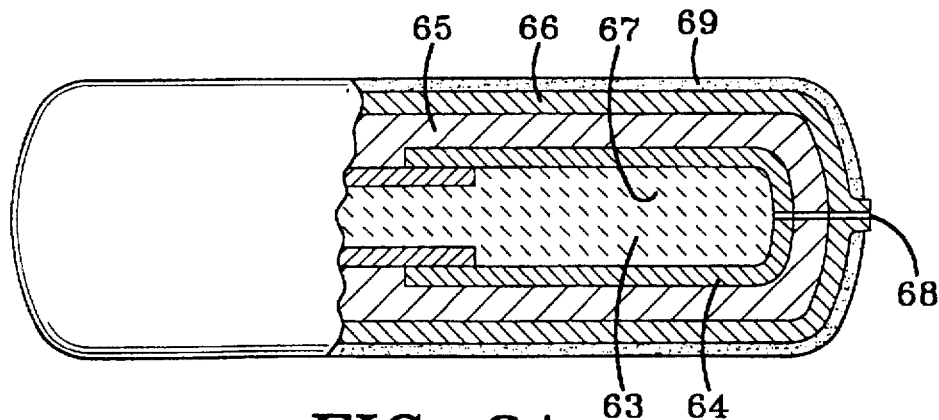
FIG. 8A is a view similar to FIG. 8 of a sustained release reservoir of the same type but with an external coating of a marker dye that is readily taken up immediately in the medium of the liquid enteral nutritional product at the outset of commencing the flow thereof through the drip chamber.

In FIG. 8A there is represented a sustained release reservoir of the type shown in FIG. 8, but with a readily soluble external coating 69 consisting of marker dye alone or admixed with one or more physiologically acceptable excipients to, preferably, mildly bind the dye to the exterior of the sustained release reservoir. Excipients such as polyvinylpyrrolidone having a weight average molecular weight in the range of about 35,000 to 50,000, mannitol, sorbitol, starch, or magnesium stearate, may be selected individually or in combination with zein or guar gum, in a total amount up to about 10 percent by weight of the coating. The marker dye coating, to be useful, is one that quickly dissolves in the medium of the liquid enteral nutritional product to provide practically immediate dye marking, preferably within ten seconds and more preferably within less than three seconds.

Figure 9:
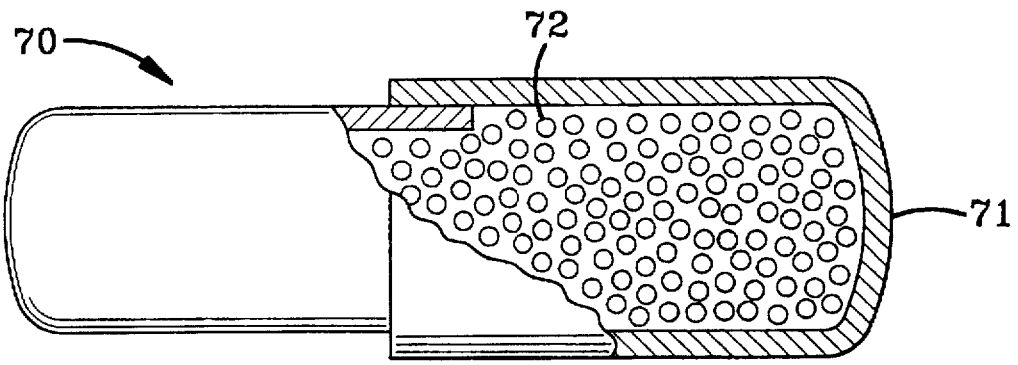
FIG. 9 is a view in front elevation, partly broken away and in section, of a readily disintegrable or soluble capsule type carrier of a useful quantity of sustained release reservoirs, of the microencapsulated particle type, the molecular sieving type, or chopped, permeable, hollow-fiber type, containing at least one physiologically acceptable marker dye that is soluble in the medium of the liquid enteral nutritional product medium within the drip chamber according to the invention.
Figure 9A:
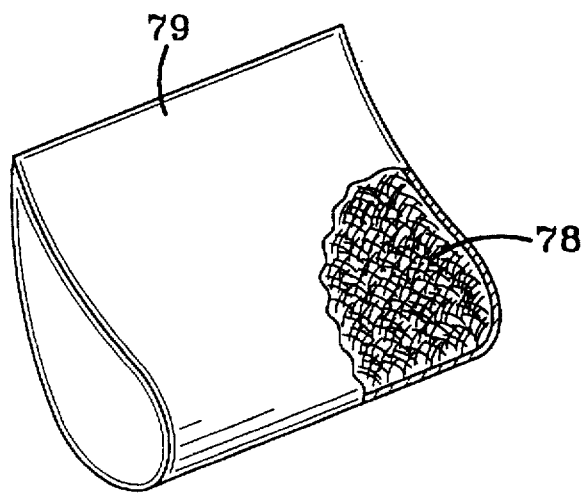
FIG. 9A is a perspective view, partly broken away and in section, of a highly permeable fibrous packet, preferably of the non-woven tea-bag type of carrier suitable for placing in a drip chamber, or other form of formulation chamber, and capable of holding a sustained release reservoir such as a tablet or osmotic driven device or capsule, or a useful quantity of sustained release reservoirs in the form of microencapsulated particles, molecular sieving type material or permeable hollow fibers, each such reservoir containing at least one physiologically acceptable marker dye that is soluble in the medium of the liquid enteral nutritional product medium within the drip chamber according to the invention.

If quick dye marking, particularly with a colorant dye, is found especially useful or helpful, it may be achieved rather simply by selecting and utilizing a feeding set in which there has been placed in the drip chamber or other formulation chamber a small amount of readily soluble and suitable colorant dye not in a sustained release dosage form, but in a fibrous packet such as the packet 79 shown in FIG. 9A. This may be done in lieu of using a dye-coated sustained release reservoir for quick coloration. Some marker dye 78, not in a sustained release dosage form, but, for example, in loose particulate form, may be placed in the fibrous packet 79 and both the packet and one of the sustained release reservoirs described above positioned adjacently together in the formulation chamber. Also, if desired, some non-sustained release colorant dye may be placed in the fibrous packet accompanied by a sustained release reservoir containing the same colorant dye for continuation of the dye marking for up to 24 hours during feeding. Generally, about 1 to about 10 mg, and preferably about 5 mg, of a colorant dye such as F.D.& C. Blue #1 dye in non-sustained release dosage form provides sufficient nearly instant visible color when flow of liquid enteral nutritional product is started through the formulation chamber.

The sustained release reservoir carrier 70 depicted in FIG. 9 is of the type in which there is provided, within a readily enteral nutritional product medium-soluble or medium-disintegrable envelope 71, a quantity of microcapsules or agglomerated molecular sieving particles 72. If microcapsules, they are microspheres each individually coated, each containing at least one physiologically acceptable marker dye that is soluble in the medium of the nutritional product, with a plurality of respective portions or fractions thereof each provided with one or more nutritional product medium-soluble or -permeable or -disintegrable coatings in a range of coating thicknesses whereby a sustained release effect is obtained. The envelope and coatings must essentially be physiologically acceptable for nutritional feeding, whether soluble in the liquid medium of the liquid enteral nutritional product or merely disintegrable into a debris carried by the flow of the medium.

If the particles are of a molecular sieving type, or a mixture of two or more molecular sieve grades, the particles should be impregnated with the marker dye or dye mixture to be used for color marking and the particles agglomerated into desired size granules or clumps that are used as such within the envelope 71 of FIG. 9 or the fibrous bag of FIG. 9A, or lightly coated with a soluble, disintegrable or permeable coating to form a sustained release reservoir per se usable according to the invention.

The sustained release reservoirs within a carrier envelope may also take the form shown in FIG. 9A of a fibrous, preferably non-woven bag 79, similar to a conventional tea bag, with a content of chopped, fine, hollow permeable fibers in place of loose particulate dye 78. Such chopped hollow fibers may be formed of permeable material such as a reconstituted cellulose or a cellulose ether or cellulose ester, capable of taking up and storing a physiologically acceptable marker dye or dye mixture and subsequently yielding it up upon contact with a flowing liquid enteral nutritional product within a drip chamber or other contact chamber. The hollow fibers 78 in FIG. 9A are carried within a highly permeable non-woven fibrous envelope 79 that is similar to a conventional tea bag.

Any mode of sustained release may be used in making a reservoir usable according to the invention so long as any soluble or disintegrable components of the coating, or a carrier envelope, are physiologically acceptable and the sustained release reservoir is capable of storing a suitable marker dye or dye mixture and releasing it into the liquid enteral nutritional product at a useful rate over a useful period of time during enteral feeding.

In a preferred embodiment of the apparatus of the invention the one or small number of reservoirs in the formulation chamber are each of the type illustrated in FIG. 8A in which each reservoir is externally coated with a soluble, or quickly disintegrable, layer of or containing about 5 mg in total of F.D.& C. Blue #1 dye. The dye coating on the reservoir provides blue coloration of the flowing enteral nutritional product within 3 seconds and the reservoir, or reservoirs collectively, provides the said blue dye at a concentration in the liquid enteral nutritional product at a sustained concentration of at least 0.075 milligrams per milliliter (mg/ml) and not more than 0.125 mg/ml, and more preferably about 0.10 mg/ml, within less than one minute and continuing up to about 1,440 minutes, during the flow of from about 0.7 ml through about 3,000 ml of the liquid nutritional product which has a viscosity of about 15 cps.

In another preferred embodiment of the apparatus of the invention, the one or more sustained release reservoirs in the formulation chamber are each of the type illustrated in FIG. 8 in which each such reservoir contains F.D.& C. Red #3 dye as the marker dye, and the reservoir or reservoirs collectively provide the fluorescing red dye in the liquid enteral nutritional product at a concentration of at least 0.01 mg/ml and not more than about 0.05 mg/ml within less than about 10 seconds and continuing up to about 1200 minutes, during the flow of from about 1.5 ml through about 3,000 ml. of the liquid enteral nutritional product which has a viscosity of about 28 cps.

In yet another preferred embodiment of the apparatus of the invention using a feeding set connected to a hanging container of liquid enteral nutritional product as shown in FIG. 2, the one or more sustained release reservoirs in the formulation chamber are each of the type illustrated in FIG. 8A in which each sustained release reservoir is externally coated with a soluble, or quickly disintegrable, layer of or containing F.D.& C. Blue #2 dye, and the reservoir, or reservoirs collectively contain a mixture of F.D.& C. Blue #2 dye and F.D. & C. Red #3 dye and provide the said blue dye at a concentration in the liquid enteral nutritional product at a concentration of at least 0.075 milligrams per milliliter (mg/ml) and not more than 0.125 mg/ml, and more preferably about 0.10 mg/ml, and the fluorescing red dye at a concentration of at least 0.01 mg/ml and not more than 0.02 mg/ml, with the blue dye appearing at at least minimum concentration within 10 seconds and the fluorescing red dye within 15 seconds and both continuing up to about 1,440 minutes, during the flow of from about 0.7 ml through about 3,000 ml of the liquid nutritional product having a viscosity of about 53 cps. The dye-marked liquid enteral nutritional product when examined under ultraviolet light visibly fluoresces.

In still another preferred embodiment of the apparatus and method of the invention a feeding set like the one shown in FIG. 2 is connected to a hangable container so as to receive the flow of a nutritional product therefrom. The container is filled with a liquid enteral nutritional product, such as PULMOCARE®, a product of the Ross Products Division of Abbott Laboratories, Columbus, Ohio having a viscosity of about 40 cps. The drip chamber of the feeding set contains an osmotic device, such as that shown in FIG. 8, containing F.D. & C. Blue #1 dye, as the sustained release reservoir in the formulation chamber. A steady flow of the liquid enteral nutritional product is commenced. The osmotically driven device provides the said blue dye in the flow of liquid enteral nutritional product at a varying concentration of at least 0.075 milligrams per milliliter (mg/ml) and not more than 0.125 mg/ml, but more predominantly about 0.10 mg/ml, with the blue dye appearing at at least minimum concentration within 10 seconds and continuing up to about 1,440 minutes, during the flow of from about 0.7 ml through about 3,000 ml of the liquid enteral nutritional product.

In yet another embodiment of the apparatus and method of the invention a feeding kit like the one shown in FIG. 1, but with a formulation chamber equipped with a foraminous plate such as that shown in FIG. 13, is connected to a hangable container so as to receive a steady flow of a nutritional product therefrom. The hangable container is filled with a liquid enteral nutritional product having a viscosity of about 12 cps., such as OSMOLITE®, a product of the Ross Products Division of Abbott Laboratories, Columbus, Ohio. The drip chamber of the feeding set contains a gelatin capsule carrier for sustained release reservoirs such as that shown in FIG. 9. Microencapsulated F.D.& C. Blue #1 dye sustained release reservoirs are contained in the thin-walled gelatin capsule carrier that is supported on the foraminous plate and disintegrates immediately in the medium of the liquid enteral nutritional product. The blue dye has been processed into a quantity of microspheres that have been divided into six portions. Five portions have been microencapsulated, having, respectively, from one to five layers of a zein coating applied to the microspheres of respective portions in order to slow down solubilizing of the dye, relatively, from portion to portion, in the medium of the liquid enteral nutritional product. The five microencapsulated portions have been blended with the uncoated microspheres and used to fill the gelatin capsule. The gelatin capsule has further been coated with a quick dissolving layer of a mixture of about 8 mg of the said blue dye and a minor amount, about three percent by weight based on the weight of the dye, of polyvinylpyrrolidone having a weight average molecular weight in the range of 35,000 to 44,500. The surface coating of the gelatin capsule provides coloration of the flowing liquid enteral nutritional product within 2 seconds and the microencapsulated microspheres provide the said blue dye in the flow of liquid enteral nutritional product at a varying concentration of at least 0.065 milligrams per milliliter (mg/ml) and not more than 0.25 mg/ml, with the blue dye appearing sufficiently quickly to maintain visible blue coloration at at least minimum concentration and continuing up to about 1,320 minutes, during the flow of from about 0.7 ml through about 2,400 ml of the liquid nutritional product.

Wherein the provision of a dye-marked liquid enteral nutritional product at a closely uniform rate over time, such as about 2 to about 30 hours or more but more usually not over 24 hours, is necessary or quite important, the osmotic pump or osmotic dosage systems are to be preferred for more uniformity of operation and less fall-off of dye release over time during a given feeding.

Figure 14:
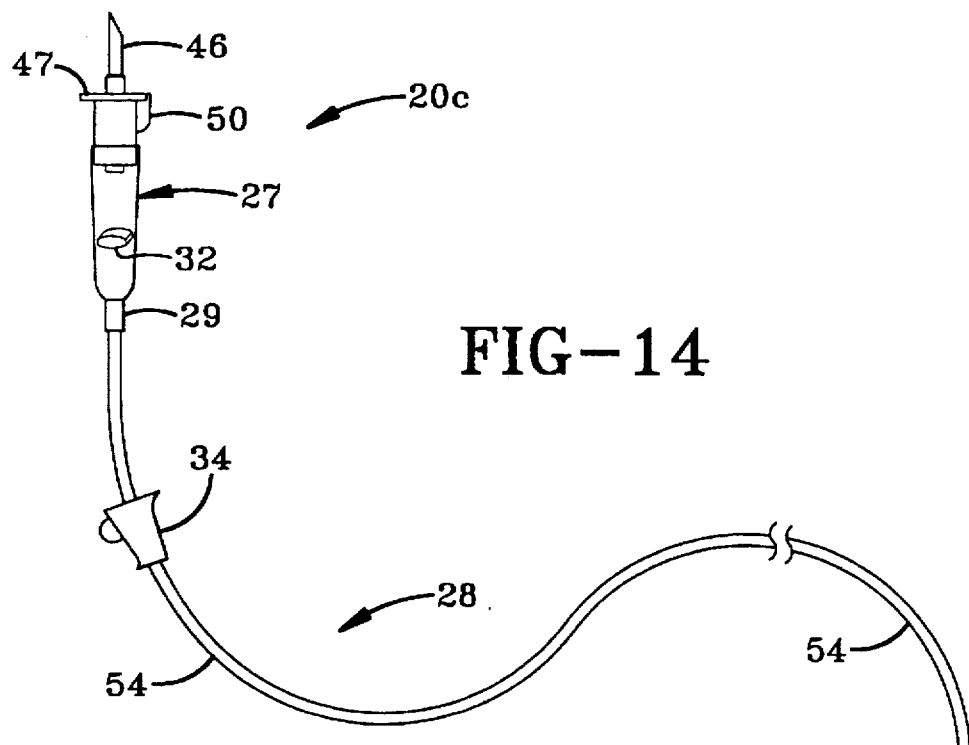
FIG. 14 is a side elevation of a kit consisting of a feeding set according to the invention, including a drip chamber loaded with a sustained release reservoir containing marker dye, and fluid communication means to connect the drip chamber with the feeding tube used to direct the dye-marked liquid enteral nutritional product to the gastrointestinal tract of a patient, including a cap for the end connector.

A feeding set, such as the kit 20 shown in FIG. 14, is conveniently provided in packaged form ready for use in feeding a liquid enteral nutritional product with a sustained release reservoir 32 containing a physiologically acceptable marker dye already placed within the drip chamber 27 serving as a formulation chamber, and the drip chamber having attached to the outlet thereof a suitable length of flexible tubing 54 serving as the major part of the communication means terminating in a conventional coupling element 30 having a cap 55, as seen in FIG. 14, which is removable for attachment of the coupling element to the inlet of a feeding tube. The kit will be selected to contain a sustained release reservoir containing a physiologically acceptable marker dye that is soluble in the medium of the liquid enteral nutritional product to be fed using the kit. The kit may also be provided with a plurality of sustained release reservoirs for use wherein a greater depth of dye marking is needed or desired in the event the flow of the nutritional product is expected to be quite rapid, or, the dye is of limited solubility in the product.

Figure 10:
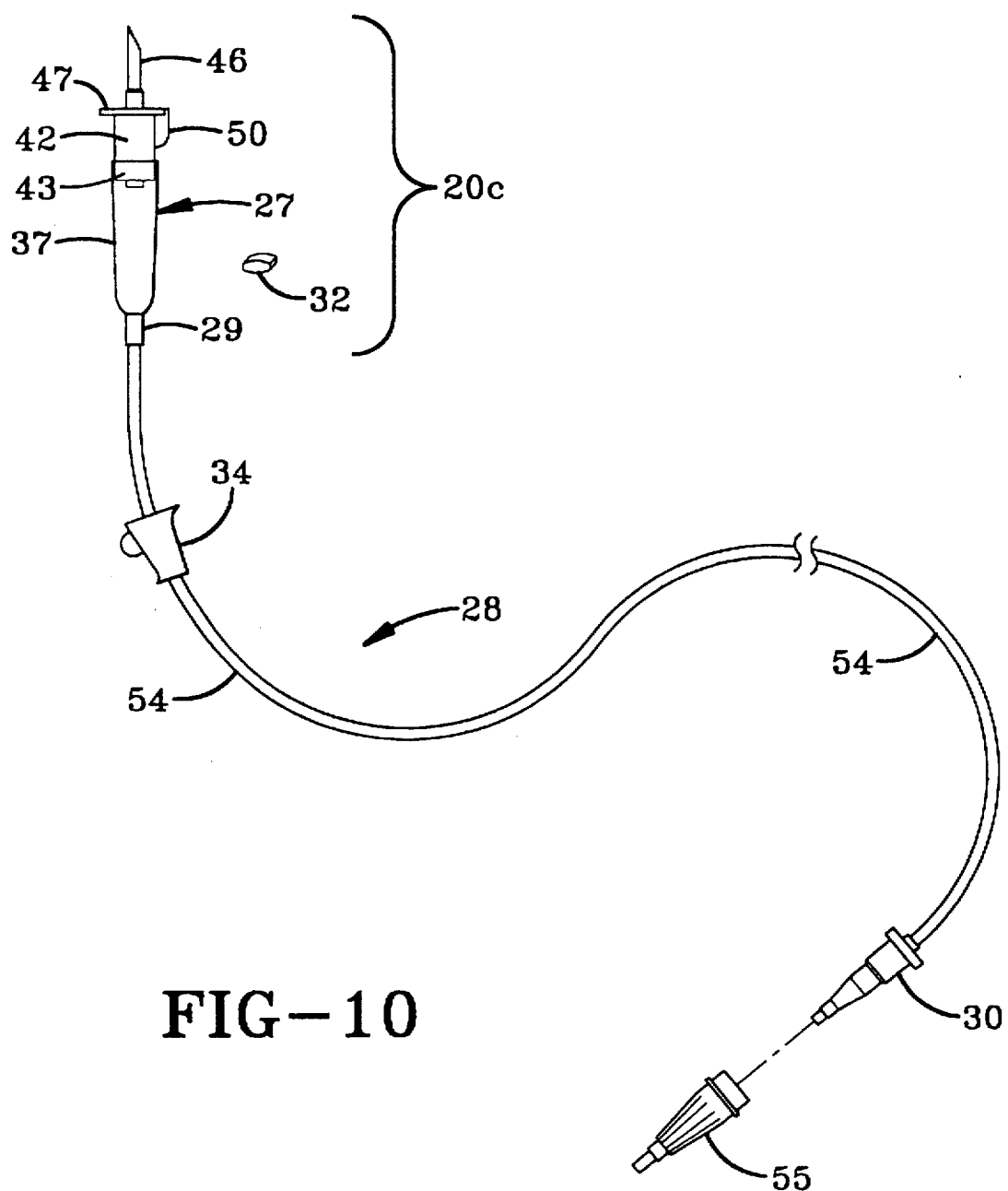
FIG. 10 is a view in side elevation of a kit useful in dye-marking a liquid enteral nutritional product during the feeding thereof, the kit including a drip chamber connected to tubing communication means to connect the kit to a feeding tube, and a sustained release reservoir containing a useful amount of a suitable marker dye or dye mixture accompanies the drip chamber ready to be emplaced therein.

A similar kit 20a, as shown in FIG. 10, includes the sustained release reservoir 32 which has not been placed in the drip chamber 27, but may be provided with a protective wrapper (not shown), if desired, until use. For example, the plug 42 of the drip chamber may be made readily removable from the chamber body 37 and reinsertable to facilitate placement of one or more sustained release reservoirs in the formulation/drip chamber.

Dye marking a liquid enteral nutritional product is broadly useful, using the apparatus and methods of the invention, whether marking solely the enteral product per se or marking the product while also adding thereto, within a formulation chamber, such as a drip chamber, one or more beneficial agents such as nutrients, medicaments, probiotics, or diagnostic agents, in either or both controlled release dosage form or non-controlled release dosage form, during enteral feeding. Controlled release is meant to include sustained release as well as delayed or intermittent release.

We claim:

1. An apparatus for liquid enteral nutritional product feeding comprising:
 - a formulation chamber having an inlet and an outlet, said inlet fluidly connected to a supply container containing a liquid enteral nutritional product having a viscosity of at least about 3 centipoises whereby said formulation chamber receives said liquid enteral nutritional product from said supply container;
 - the formulation chamber further comprising at least one physiologically acceptable marker dye, the at least one marker dye being contained within at least one sustained release reservoir positioned within the formulation chamber so as to be in physical contact with said liquid enteral nutritional composition in said formulation chamber, the at least one marker dye being soluble in the liquid enteral nutritional product, said at least one sustained release reservoir containing marker dye being a means for providing and dispensing marker dye into said liquid enteral nutritional product when the sustained release reservoir is physically contacted thereby during the feeding thereof to a patient over a time period of at least about two hours; and
 - fluid communication means capable of operatively connecting the outlet of the formulation chamber to a device that feeds the dye-marked liquid enteral nutritional product into the gastrointestinal tract of a patient.

2. The apparatus of claim 1 wherein the at least one sustained release reservoir is confined within a highly porous fibrous packet.

3. The apparatus of claim 2 wherein the fibrous packet contains additional marker dye that is not in a sustained release reservoir.

4. The apparatus of claim 2 wherein the fibrous packet is of non-woven construction.

5. The apparatus of claim 1 wherein the at least one physiologically acceptable marker dye is a blue dye or a mixture of a plurality of blue dyes.

6. The apparatus of claim 5 wherein the at least one physiologically acceptable marker dye is F.D & C. Blue #1 or F.D.& C. Blue #2.

7. The apparatus of claim 1 wherein the marker dye is a colorant dye visible under white light.

8. The apparatus of claim 1 wherein the marker dye is a fluorescing dye.

9. The apparatus of claim 1 wherein at least one sustained release reservoir in the formulation chamber is externally coated with readily dispersible colorant dye.

10. The apparatus of claim 1 wherein the formulation chamber is a drip chamber.

11. The apparatus of claim 1 wherein the formulation chamber contains a plurality of sustained release reservoirs containing at least one physiologically acceptable marker dye.

12. The apparatus of claim 1 wherein the liquid enteral nutritional product is an aqueous composition and each of the at least one sustained release reservoirs containing marker dye is a water soluble ingredient delivery device containing at least one water soluble marker dye comprising:
 at least one inner mass transfer conductor;
 the at least one water soluble marker dye being disposed in the at least one inner mass transfer conductor, and the at least one inner mass transfer conductor being permeable to the passage of the at least one water soluble marker dye; and
 a membrane surrounding the at least one inner mass transfer conductor, which membrane releases at least a useful amount of the at least one water soluble marker dye into the liquid enteral nutritional product employed when the liquid enteral nutritional product is passed over the membrane and administered enterally to a patient.

13. The apparatus of claim 1 wherein each of the at least one sustained release reservoirs containing a marker dye is an osmotically driven device containing at least one physiologically acceptable marker dye that is soluble in the medium of the liquid enteral nutritional product, the device comprising:

a body wall defining an enclosed elongated cavity with first and second ends;

a piston longitudinally slideable in the cavity while touching the body wall laterally thereof;

the piston defining first and second zones within the cavity, the first zone being filled with a hydro-active substance and the second zone being filled with the at least one physiologically acceptable marker dye in liquid or solution form;

the body wall having first and second portions, the first portion surrounding the first zone and first end of the cavity and a portion of the adjacent second zone and being of a moisture permeable membrane, and the second portion of the body wall surrounding at least the second end of the cavity and overlapping the first portion and being of a membrane that is non-permeable to the liquid enteral nutritional product, with an orifice formed therethrough at the second end of the cavity, each portion of the body wall being of a material that maintains its integrity for at least 24 hours in the presence of moisture.

14. The apparatus of claim 1 wherein the liquid enteral nutritional product is an aqueous composition and each of the at least one sustained release reservoirs containing marker dye is an osmotically driven device, the device comprising:

a capsule formed by an exterior wall made up, at least in part, by a semipermeable composition that maintains its integrity in the presence of an aqueous fluid, the exterior wall surrounding a hydro-activated layer comprising a hydro-activated swellable composition or a hydro-activated composition that occupies space at a controlled rate, and an inner capsule surrounded by the hydro-activated layer and communicating with a lumen extending to the exterior of the outer capsule, the inner capsule containing at least a useful amount of the at least one water soluble marker dye in liquid formulation form and the wall of the inner capsule being substantially non-permeable to the liquid enteral nutritional product.

15. The apparatus of claim 1 wherein there are a plurality of sustained release reservoirs containing a marker dye and substantially each such sustained release reservoir comprises a microsphere particle containing the at least one physiologically acceptable marker dye, the respective particles having from none to about six microencapsulating coating thicknesses that gradually dissolve and release the at least one physiologically acceptable marker dye from within the particles when contacted over time by the liquid enteral nutritional product.

16. The apparatus of claim 1 wherein the at least one sustained release reservoir is an agglomerated molecular sieving type impregnated with the at least one physiologically acceptable marker dye, the agglomerated molecular sieving gradually yielding up the at least one physiologically acceptable marker dye when contacted over time by the liquid enteral nutritional product.

17. The apparatus of claim 1 wherein the at least one sustained release reservoir is provided with an exterior layer that substantially maintains its integrity for at least the useful life of the reservoir while exposed to liquid enteral nutritional product, and the reservoir is in the shape of a rectangular solid.

18. The apparatus of claim 1 wherein the at least one sustained release reservoir is confined within a mesh bag within the formulation chamber.

19. The apparatus of claim 1 wherein the at least one sustained release reservoir is confined within a foraminous bag within the formulation chamber.

20. The apparatus of claim 1 wherein the formulation chamber contains a soluble physiologically acceptable marker dye not in a sustained release reservoir in addition to at least one sustained release reservoir containing marker dye.

21. The apparatus of claim 1 wherein the at least one sustained release reservoir is supported within the formulation chamber on a foraminous plate or grid.

22. An apparatus for liquid enteral nutritional product feeding comprising:

a formulation chamber having an inlet and an outlet, said inlet fluidly connected to a supply container containing a liquid enteral nutritional product having a viscosity of at least about 3 centipoises whereby said formulation chamber receives said liquid enteral nutritional product from said supply container;

the formulation chamber further comprising at least one sustained release reservoir disposed within the formulation chamber so as to be in physical contact with said liquid enteral nutritional product in said formulation chamber, said at least one sustained release reservoir disposed in the formulation chamber, one of said at least one sustained release reservoirs being an osmotically driven device containing at least one physiologically acceptable marker dye that is soluble in said liquid enteral nutritional product when said liquid enteral nutritional product flows in contact with the osmotically driven device over a time period of at least about two hours; and fluid communication means capable of operatively connecting the outlet of the formulation chamber to a device that feeds the dye-marked liquid enteral nutritional product into the gastrointestinal tract of a patient.

23. The apparatus of claim 22 wherein the osmotically driven device is in the form of a capsule formed by an exterior wall made up, at least in part, by a semipermeable composition that maintains its integrity in the presence of an aqueous fluid, the exterior wall surrounding a hydro-activated layer comprising a hydro-activated swellable composition or a hydro-activated composition that occupies space at a controlled rate, and an inner capsule surrounded by the hydro-activated layer and communicating with a lumen extending to the exterior of the outer capsule, the inner capsule containing the at least one marker dye in liquid formulation form and the wall of the inner capsule being substantially non-permeable to the liquid enteral nutritional product.

24. The apparatus of claim 23 wherein the marker dye is a colorant dye visible in the liquid enteral nutritional product under white light.

25. The apparatus of claim 24 wherein the colorant dye is F.D.& C. #1 Blue dye or F.D.& C. #2 Blue dye.

26. The apparatus of claim 23 wherein the marker dye is a fluorescing dye.

27. The apparatus of claim 23 wherein the marker dye is a mixture of a colorant dye and a fluorescing dye.

28. A drip chamber comprising a sustained release reservoir disposed within said drip chamber, said sustained release reservoir containing at least a useful amount of at least one water soluble marker dye that is physiologically acceptable for enteral use, said sustained release reservoir constructed to release into a liquid enteral nutritional product having a viscosity of at least about 3 centipoises said at least one water soluble marker dye over a time period of at least about two hours.

29. A drip chamber as in claim 28 having disposed therein at least one additional sustained release reservoir, said at least one additional sustained release reservoir containing at least a useful amount of at least one water soluble marker dye that is physiologically acceptable for enteral use, said at least one additional sustained release reservoir constructed to release said at least one water soluble marker dye into a liquid enteral nutritional product having a viscosity of at least about 3 centipoises said at least one water soluble marker dye over a time period of at least about two hours.

30. A kit for feeding a liquid enteral nutritional product into the gastrointestinal tract of a patient, said kit comprising:

a formulation chamber having an inlet and an outlet, said inlet fluidly connected to a supply container containing a liquid enteral nutritional product having a viscosity of at least about 3 centipoises whereby said formulation chamber receives said liquid enteral nutritional product from said supply container, the formulation chamber having therein a means for supporting at least one sustained release reservoir in a position so as to be wetted by or immersed in said liquid enteral nutritional product in said formulation chamber;

at least one sustained release reservoir containing at least one physiologically acceptable marker dye that is soluble in said liquid enteral nutritional product, said at least one sustained release reservoir mounted on said means for supporting, the at least one physiologically acceptable marker dye being present and sustainedly releasable in at least a sufficient amount to impart a coloration, visible under either daylight or ultraviolet light, to said liquid enteral nutritional product for a period of at least about two hours; and fluid communication means capable of operatively connecting the outlet of the formulation chamber to a device that feeds the dye-marked liquid enteral nutritional product into the gastrointestinal tract of a patient.

* * * * *